(12) United States Patent
Dhar et al.

(10) Patent No.: US 7,375,237 B2
(45) Date of Patent: May 20, 2008

(54) PYRROLIZINE COMPOUNDS USEFUL AS ANTI-INFLAMMATORY AGENTS

(75) Inventors: T. G. Murali Dhar, Newtown, PA (US); Dharmpal S. Dodd, Princeton, NJ (US); Dominique Potin, Epone (FR); Michele Launay, Rueil Malmaison (FR)

(73) Assignees: Bristol-Myers Squibb Company, Princeton, NJ (US); Cerep SA, Rueil-Malmaison (FR)

( * ) Notice: Subject to any disclaimer, the term of this patent is extended or adjusted under 35 U.S.C. 154(b) by 273 days.

(21) Appl. No.: 11/206,558

(22) Filed: Aug. 18, 2005

(65) Prior Publication Data

US 2006/0052434 A1    Mar. 9, 2006

Related U.S. Application Data

(60) Provisional application No. 60/602,455, filed on Aug. 18, 2004.

(51) Int. Cl.
*C07D 209/32* (2006.01)
*A01N 43/38* (2006.01)

(52) U.S. Cl. .................................... 548/512; 514/413
(58) Field of Classification Search ............ None
See application file for complete search history.

(56) References Cited

U.S. PATENT DOCUMENTS 5,683,965 A    11/1997    Bachmann et al.

FOREIGN PATENT DOCUMENTS

| EP | 0 442 077 | 11/1995 |
|---|---|---|
| JP | 2000-293276 | 9/2000 |
| WO | WO 98/39303 | 9/1998 |
| WO | WO 99/20617 | 4/1999 |
| WO | WO 99/20618 | 4/1999 |
| WO | WO 99/49856 | 10/1999 |
| WO | WO 00/21920 | 4/2000 |
| WO | WO 03/029245 | 4/2003 |

OTHER PUBLICATIONS

Dodd et al., "Design of LFA-1 antagonists based on a 2,3-dihydro-1h-pyrrolizin-5(1aH)-one scaffold", Bioorg. Med Chem Lett, 17, 2007, 1908-1911.*
Giblin et al., "LFA-1 as a Key regulator of immune function: approaches toward the development of LFA-1 based therapeutics", current pharm design, 2006, 12, 2771-2795.*
Barnes, P.J.; "Mediators of Chronic Obstructive Pulmonary Disease", Pharmacol. Rev. (2004), vol. 56, p. 515-548.*
Parlier et al., Organometallics, 14, 1995, 2761.*
http://www.health.harvard.edu/special_health_reports/Chronic_Obstructive_Pulmonary_Disease.htm.*
http://www.mayoclinic.com/health/alzheimers-disease/DS00161/DSECTION=3.*
http://www.medindia.net/patients/patientinfo/Alzheimers_treatment.htm.*
FACT Sheet , Alzheimers association (2 pages).*
http://www.icos.com/popUps/pop_ic747.html.*
Parlier, A. et al., "Reaction of Aminocarbene Complexes of Chromium with Alkynes. 5. Influence of the Ring Size on the Product Distribution. Formation of Pyrroles from Pyrrolidine and Its Derivative-Substituted Carbene Complexes", Organometallics, vol. 14, No. 6, pp. 2760-2774 (1995).
Rudler, H. et al., "Unexpected ring opening of cycloaminocarbene complexes of chromium upon alkyne insertion reactions", Journal of Organometallic Chemistry, vol. 358, pp. 245-272 (1988).
Anderson, D.C. et al., "Leukocyte LFA-1, OKM1, p150,95 deficiency syndrome: functional and biosynthetic studies of three kindreds", Federation Proceedings, vol. 44, No. 10, pp. 2671-2677 (1985).
Diamond, M.S. et al., "The dynamic regulation of integrin adhesiveness", Current Biology, vol. 4, No. 6, pp. 506-517 (1994).
Górski, A., "The roll of cell adhesion molecules in immunopathology", Immunology Today, vol. 15, No. 6, pp. 251-255 (1994).
Sanfilippo, P.J. et al., "Novel Thiazole Based Heterocycles as Inhibitors of LFA-1/ICAM-1 Mediated Cell Adhesion", J. Med. Chem., vol. 38, No. 7, pp. 1057-1059 (1995).

* cited by examiner

*Primary Examiner*—Rebecca Anderson
*Assistant Examiner*—Sun Jae Y Loewe
(74) *Attorney, Agent, or Firm*—Laurelee A. Duncan

(57) ABSTRACT

Pyrrolizine compounds having the formula (I),

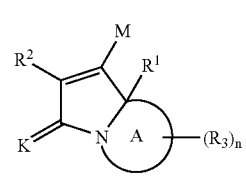

or pharmaceutically-acceptable salts thereof, are effective in treating inflammatory or immune diseases, where A is a four- to seven-membered saturated ring, K is O or S, and $R^1$, $R^2$, $R^3$ n, and M are defined in the specification.

5 Claims, No Drawings

PYRROLIZINE COMPOUNDS USEFUL AS ANTI-INFLAMMATORY AGENTS

This application claims priority from U.S. Provisional Application 60/602,455 filed Aug. 18, 2004 which is incorporated herein by reference.

FIELD OF THE INVENTION

The present invention relates to pyrrolizine compounds, pharmaceutical compositions containing them, and methods of using such compounds in treating inflammatory or immune diseases.

BACKGROUND OF THE INVENTION

Cells adhere to other cells and to substrates through specific, regulated processes that are critical to various biological functions. The proper functioning of the immune system, for example, is dependent upon adhesive interactions and cell migration. A key event in an immune response involves the migration of leukocytes to a disease site. During an inflammatory response, leukocytes are recruited to the site of injury and extravasated by a series of cellular interactions involving cell-cell and cell-substrate adhesion.

One family of molecules that serve an important adhesive function are integrins. Integrins are expressed on cell surfaces and function in cell-cell and cell-substrate adhesion. Integrins are alpha-beta heterodimers: each integrin has an alpha ($\alpha$) subunit non-covalently binded to a beta ($\beta$) subunit. When activated, integrins bind to extracellular ligands and induce adhesion (the expression of integrins on a cell surface alone is inadequate for adhesion—they must be activated to become adhesive). The integrin activation state is transient, such that there is a rapid flux between adhesive and non-adhesive states which is important for cell movement, e.g., a cell is endowed with the ability to rapidly adhere to various cell surfaces and matrices and to migrate among cells and tissue.

There are four known integrins having a $\beta_2$ or CD18 subunit which comprise the CD11/CD18 integrin sub-family, namely, Lymphocyte Function-associated Antigen 1 (LFA-1) (CD11a/CD18 or $\alpha_L\beta_2$); Macrophage Antigen 1 (Mac-1) (CD11b/CD18 or $\alpha_M\beta_2$); p150,95 (CD11c/CD18 or $\alpha_X\beta_2$); and $\alpha_D\beta_2$. The CD11/CD18 family of integrins are also referred to as Leukointegrins as they are expressed on the surface of various leukocyte cells, and they mediate a number of inflammation-related cellular interactions. See Diamond et al., "*The Dynamic Regulation of Integrin Adhesiveness,*" *Current Biology*, Vol. 4 (1994) at pp. 506-532.

Ligands to LFA-1 and Mac-1 comprise the intercellular adhesion molecule (ICAM) ICAM-1. LFA-1, the primary CD11/CD18 integrin, also binds with ICAM-2 and ICAM-3. ICAMs are found on endothelium cells, leukocytes, and other cell types, and their interaction with CD11/CD18 integrins is critical to immune system function. The interaction between the CD18 integrins, particularly LFA-1, and ICAMs mediates antigen presentation, T-cell proliferation, and adhesion between the endothelium and activated leukocytes which is necessary for leukocytes to migrate from the circulatory system into tissue. A condition termed "Leukocyte Adhesion Deficiency" has been identified in patients having a severe deficiency in CD 18 integrins. These patients are unable to mount a normal inflammatory or immune response; they suffer from disorders such as recurrent infections, poor wound healing, granulocytosis, progressive periodontitis, and umbilical cord separation. See Anderson et al., "*Leukocyte LFA-*1*, OKMI*, p 150,95 *Deficiency Syndrome: Functional and Biosynthesis Studies of Three Kindreds,*" *Fed. Proc.*, Vol. 44 (1985), pp. 2671-2677.

While sufficient levels of CD18 integrins interacting with ICAMs are needed to mount a normal immune response, significant cellular and tissue injury can result in chronic inflammatory states where there is an inappropriate influx of leukocytes to the disease site. Continuous recruitment of leukocytes from blood vessels into inflamed tissue, as in chronic inflammatory states, can perpetuate tissue injury and lead to excessive fibrous repair and autoimmune disease. Thus, inhibition of the interaction between LFA-1 and/or Mac-1 and their ICAMs can be advantageous in treating inflammatory or immune disease. For example, monoclonal antibody blockade of either ICAM or LFA-1 has been shown to prevent the migration of leukocytes into tissue and the subsequent development of inflammatory disease in animal models of rheumatoid arthritis, inflammatory bowel disease, and pulmonary inflammation (e.g., asthma). Knockout mice deficient in ICAMs have reduced susceptibility to induced arthritis, ischemia injury, impaired lung inflammatory responses, and increased tolerance to transplantations (e.g. heart grafts). See Anderson, supra. Antibodies blocking the ICAM-LFA-1 interaction reportedly suppress cardiac allograft rejection and islet cell xenograft rejection in animal models. See Gorski, "*The Role of Cell Adhesion Molecules in Immunopathology,*" *Immunology Today*, Vol. 15 (1994), at pp. 251-255.

Compounds inhibiting CD 18 integrins, ICAMs, or the LFA-1:ICAM interaction could potentially demonstrate a wide range of utilities in treating inflammatory or immune diseases. Blockage of LFA-1 reportedly inhibits the influx of leukocytes in almost every system, including the skin, peritoneum, synovium, lung, kidney and heart, and blocking ICAM-1 would be expected to have similar effects. Also, present therapies for many inflammatory or immune diseases have drawbacks. There is an interest in providing consumers with drugs having increased effectiveness and fewer side effects. For example, current treatments for asthma include $\beta_2$-agonists, inhaled corticosteroids, and $LTD_4$ antagonists. However, $\beta_2$-agonists have limited efficacy and inhaled corticosteroids raise safety concerns. To treat psoriasis, current therapies include PUVA, methotrexate, cyclosporin A, and topical treatments. The first three of those therapies raise toxicity issues over long-term (6-9 month) use, whereas topical treatments have limited efficacy. Additionally, these treatments typically are applied only in response to flares and not as a prophylaxis measure.

Accordingly, there is great interest in developing Leukointegrin or ICAM antibodies and antagonists of Leukointegrins and/or ICAMs. Hydantoin-based compounds are active LFA-1/ICAM inhibitors. See Intern. Pub. No. WO WO/03029245, "Spiro-Hydantoin Compounds Useful as Anti-Inflammatory Agents" filed by Applicants. Thiadiazole-based compounds reportedly inhibit LFA-1 and Mac-1 binding with ICAM-1 and are claimed to be useful as anti-inflammatory agents. See Intern. Pub. No. WO 99/20, 618, "Thiadiazole Amides Useful as Anti-Inflammatory Agents" filed by Pharmacia & Upjohn Co. (See also WO 99/20,617, also to Pharmacia and Upjohn.) Thiazole compounds linked to phenyl and pyrazole rings are claimed to be active LFA-1/ICAM inhibitors. Sanfilippo et al., "*Novel Thiazole Based Heterocycles as Inhibitors of LFA-*1*/ICAM-*1 *Mediated Cell Adhesion,*" *J. Med. Chem.* Vol. 38 (1995) at pp.1057-1059. A series of small molecules comprising 1-(3,5 dichlorophenyl) imidazolidines are claimed to be antagonists to the binding of ICAMs with CD18 integrins.

See Intern. Pub. No. WO9839303, "Small Molecules Useful in the Treatment of Inflammatory Disease," filed by Boehringer Ingelheim Pharmaceuticals, Inc. A series of compounds comprising various benzylamines and 2-bromobenzoyltryptophan are claimed to be antagonists to LFA-1/ICAM-1 receptor binding. See Intern. Pub. No. WO99/49,856, "Antagonists for Treatment of CD11/CD18 Adhesion Receptor Mediated Disorders," filed by Genentech, Inc. See also Intern. Pub. No. WO 00/21,920, "Diaminopropionic Acid Derivatives," filed by Hoffmann-La Roche Inc., disclosing a series of compounds claimed to block ICAM activity and have particular utility in treating reperfusion injury following acute myocardial infarction.

Compounds containing a pyrrolizine core are disclosed in JP 2000239276 to Nippon Soda Co. for use as herbicides; in U.S. Pat. No. 5,683,965 to Bayer A.-G. for use as pesticides; in EP 442077 B1 to Bayer A.-G. for use as insecticides, acaricides and herbicides; and as chemical intermediates in two articles by Parlier et al. See *J. of Organometallic Chemistry* (1988), 358 at pp. 1-3, 245-72 and *Organometallics* (1995), 14(6), at pp. 2760-74.

As may be appreciated, those in the field of pharmaceutical research continue to seek to develop new compounds and compositions for treating inflammatory or immune disease such as inhibitors of Leukointegrins and/or ICAMs. Particularly in the area of immune response, many individuals respond differently to different drugs. Thus, there is an interest in providing consumers not only with pharmaceutical compounds and compositions demonstrating increased effectiveness and reduced side-effects but also different structures or mechanisms of action to provide consumers with a choice of options.

Each of the patents, patent applications and publications referenced above and hereinafter is incorporated herein by reference.

SUMMARY OF THE INVENTION

The present invention provides methods for treating inflammatory or immune disease comprising administering to a patient in need of such treatment an effective amount of at least one compound having the formula (I):

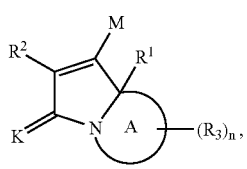

(I)

or a pharmaceutically-acceptable salt, enantiomer, or diastereomer, thereof, wherein:

K is O or S;

M is hydrogen, halogen, nitro, cyano, alkyl, substituted alkyl, alkenyl, alkynyl, $OR^{14}$, $CO_2R^6$, $C(=O)R^6$, $C(=O)NR^6R^7$, $NR^6C(=O)R^7$, $NR^6C(=O)OR^7$, $S(O)_qR^6$, $NR^6SO_2R^7$, $SO_2NR^6R^7$, $NHCH(alkyl)CO_2R^6$, aryl, heteroaryl, heterocyclo, cycloalkyl, or substituted cycloalkyl;

A is a fully or partially saturated 4- to 7-membered heterocyclo ring (preferably A is a saturated 5- or 6-membered heterocyclo ring, especially a saturated nitrogen containing 5-membered ring);

$R^1$ is $(CH_2)_r$-Z, wherein Z is aryl, heteroaryl, cycloalkyl, or heterocyclo and each Z group is substituted, where valence allows, by zero to three $R^{10}$ (preferably $R^1$ is $(CH_2)_r$-Z, wherein Z is phenyl, substituted where valence allows, by zero to three $R^{10}$);

$R^2$ is $(CH_2)_p$—X, wherein X is aryl, heteroaryl, cycloalkyl, or heterocyclo and each X group is substituted, where valence allows, by zero to three $R^{11}$ (preferably $R^2$ is phenyl substituted with zero to two $R^{11}$, or pyridyl substituted with zero to two $R^{11}$);

$R^3$ is (i) attached to any available carbon or nitrogen atom of ring A and at each occurrence is selected independently of other $R^3$ from halogen, alkyl, substituted alkyl, alkenyl, alkynyl, nitro, cyano, oxo, $OR^8$, $NR^8R^9$, $CO_2R^8$, $C(=O)R^8$, $C(=O)NR^8R^9$, $NR^8C(=O)R^9$, $NR^8C(=O)OR^9$, —OC$(=O)R^8$, —OC$(=O)NR^8R^9$, $S(O)_qR^8$, $NR^8SO_2R^9$, $SO_2NR^8R^9$, aryl, heteroaryl, heterocyclo, cycloalkyl, and substituted cycloalkyl; or (ii) a first group $R^3$ and a second group $R^3$, wherein the first group $R^3$ and the second group $R^3$ are attached to two available adjacent atoms of ring A and together form a five- to six-membered cycloalkyl, substituted cycloalkyl, heterocyclo, aryl, or heteroaryl, each of which is fused to ring A;

$R^6$ and $R^7$ are i) independently selected from hydrogen, alkyl, substituted alkyl, alkenyl, alkynyl, cycloalkyl, substituted cycloalkyl, aryl, heteroaryl, and heterocyclo; or (ii) are taken together form a heterocyclo ring;

$R^8$ and $R^9$ at each occurrence are (i) independently selected from hydrogen, alkyl, substituted alkyl, alkenyl, alkynyl, cycloalkyl, substituted cycloalkyl, aryl, heteroaryl, and heterocyclo; or (ii) taken together form a heterocyclo ring;

$R^{10}$ and $R^{11}$ at each occurrence are selected independently from halogen, alkyl, substituted alkyl, alkenyl, alkynyl, nitro, cyano, oxo, $OR^{12}$, $NR^{12}R^{13}$, $CO_2R^{12}$, and $C(=O)R^{12}$;

$R^{12}$ and $R^{13}$ at each occurrence, are i) selected independently from hydrogen, alkyl, substituted alkyl, alkenyl, alkynyl, cycloalkyl, substituted cycloalkyl, aryl, heteroaryl, and heterocyclo; or (ii) are taken together form a heterocyclo ring;

$R^{14}$ is selected from alkyl, substituted alkyl, alkenyl, alkynyl, cycloalkyl, substituted cycloalkyl, aryl, heteroaryl, and heterocyclo;

n is 0, 1, 2 or 3;

p is 0, 1, 2 or 3;

q is 0, 1, 2, or 3; and r is 0, 1, 2 or 3.

The present invention is also directed to compounds within the scope of formula (I) having the formula (Ia)

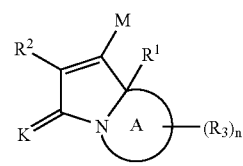

(Ia)

or a pharmaceutically-acceptable salt, enantiomer, or diastereomer, thereof, wherein:

K is O or S;

M is hydrogen, halogen, nitro, cyano, alkyl, substituted alkyl, alkenyl, alkynyl, $OR^{14}$, $CO_2R^6$, $C(=O)R^6$, $C(=O)NR^6R^7$, $NR^6C(=O)R^7$, $NR^6C(=O)OR^7$, $S(O)_qR^6$, $NR^6SO_2R^7$, $SO_2NR^6R^7$, $NHCH(alkyl)CO_2R^6$, aryl, heteroaryl, heterocyclo, cycloalkyl, or substituted cycloalkyl;

A is a fully or partially saturated 4- to 7-membered heterocyclo ring;

$R^1$ is $(CH_2)_r$-Z, wherein Z is aryl, heteroaryl, cycloalkyl, or heterocyclo and each Z group is substituted, where valence allows, by zero to three $R_{10}$;

$R^2$ is $(CH_2)_p$—X, wherein X is aryl, heteroaryl, cycloalkyl, or heterocyclo and each X group is substituted, where valence allows, by zero to three $R_{11}$;

$R^3$ is (i) attached to any available carbon or nitrogen atom of ring A and at each occurrence is selected independently of other $R^3$ from halogen, alkyl, substituted alkyl, alkenyl, alkynyl, nitro, cyano, oxo, $OR^8$, $NR^8R^9$, $CO_2R^8$, $C(=O)R^8$, $C(=O)NR^8R^9$, $NR^8C(=O)R^9$, $NR^8C(=O)OR^9$, —OC$(=O)R^8$, —OC$(=O)NR^8R^9$, $S(O)_qR^8$, $NR^8SO_2R^9$, $SO_2NR^8R^9$, aryl, heteroaryl, heterocyclo, cycloalkyl, and substituted cycloalkyl; or (ii) a first group $R^3$ and a second group $R^3$, wherein the first group $R^3$ and the second group $R^3$ are attached to two available adjacent atoms of ring A and together form a five- to six-membered cycloalkyl, substituted cycloalkyl, heterocyclo, aryl, or heteroaryl, each of which is fused to ring A;

$R^6$ and $R^7$ are i) independently selected from hydrogen, alkyl, substituted alkyl, alkenyl, alkynyl, cycloalkyl, substituted cycloalkyl, aryl, heteroaryl, and heterocyclo; or (ii) are taken together form a heterocyclo ring;

$R^8$ and $R^9$ at each occurrence are (i) independently selected from hydrogen, alkyl, substituted alkyl, alkenyl, alkynyl, cycloalkyl, substituted cycloalkyl, aryl, heteroaryl, and heterocyclo; or (ii) taken together form a heterocyclo ring;

$R^{10}$ and $R^{11}$ at each occurrence are selected independently from halogen, alkyl, substituted alkyl, alkenyl, alkynyl, nitro, cyano, oxo, $OR^{12}$, $NR^{12}R^{13}$, $CO_2R^{12}$, and $C(=O)R^{12}$;

$R^{12}$ and $R^{13}$ at each occurrence, are i) selected independently from hydrogen, alkyl, substituted alkyl, alkenyl, alkynyl, cycloalkyl, substituted cycloalkyl, aryl, heteroaryl, and heterocyclo; or (ii) are taken together form a heterocyclo ring;

$R^{14}$ is selected from alkyl, substituted alkyl, alkenyl, alkynyl, cycloalkyl, substituted cycloalkyl, aryl, heteroaryl, and heterocyclo;

n is 0, 1, 2 or 3;
p is 0, 1, 2 or 3;
q is 0, 1, 2, or 3; and
r is 1, 2 or 3.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth.

The term "substituted alkyl" refers to an alkyl group as defined above having one, two, or three substituents selected from the group consisting of halo (e.g., trifluoromethyl), alkenyl, alkynyl, nitro, cyano, amino, oxo, hydroxy, alkoxy, alkylthio, —NH(alkyl), —NH(cycloalkyl), —N(alkyl)$_2$, —NHSO$_2$, —N(alkyl)SO$_2$, —NHSO$_2$(alkyl), —NHSO$_2$(aryl), —N(alkyl)SO$_2$(alkyl), —N(alkyl)SO$_2$(aryl), —SO$_2$(alkyl), —SO$_2$(aryl), —SO$_2$N(aryl)(alkyl), —SO$_2$N(alkyl)$_2$, —CO$_2$H, —C(=O)H, —CO$_2$-alkyl, —C(=O)alkyl, —C(=O)aryl, —C(=O)NH$_2$, —C(=O)NH(alkyl), —C(=O)NH(cycloalkyl), —C(=O)N(alkyl)$_2$, —NH—CH$_2$—CO$_2$H—NH—CH(alkyl)-CO$_2$H, —NH—CH$_2$—CO$_2$-alkyl, —NH—CH(alkyl)-CO$_2$-alkyl, keto, =N—OH, =N—O-alkyl, aryl, heteroaryl, heterocyclo, cycloalkyl, and substituted cycloalkyl, including phenyl, benzyl, phenylethyl, phenyloxy, and phenylthio. When a substituted alkyl includes an aryl, heterocyclo, or heteroaryl substituent, said ringed systems are as defined below and thus may have zero, one, two, or three substituents, also as defined below.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkoxy" refers to an alkyl group as defined above having one, two or three oxygen atoms (—O—) in the alkyl chain. For example, the term "alkoxy" includes the groups —O—$C_{1-12}$alkyl, —$C_{1-6}$alkylene-O—$C_{1-6}$alkyl, —$C_{1-4}$alkylene-O—$C_{1-4}$alkylene-O—$C_{1-4}$alkyl, O—$C_{1-4}$alkylene-O—$C_{1-4}$alkylene-O—$C_{1-4}$alkyl, and so forth.

The term "thioalkyl" or "alkylthio" refers to an alkyl group as defined above bonded through one or more sulfur (-S-) atoms. For example, the term "thioalkyl" or "alkylthio" includes the groups —S—$C_{1-12}$alkyl, —S—$C_{1-6}$alkylene-S—$C_{1-6}$alkyl, etc.

The term "amino" refers to NH$_2$.

The term "aminoalkyl" refers to an alkyl group as defined above bonded through one or more nitrogen (—NH—) groups. For example, the term "aminoalkyl" includes the groups —N—$C_{1-2}$alkyl, —N—$C_{1-6}$alkylene-N—$C_{1-6}$alkyl, etc. The term aminoalkyl refers to straight and branched chain groups and thus, for example, includes the groups —NH($C_{1-12}$alkyl) and —NH($C_{1-6}$alkyl)$_2$. When a subscript is used with reference to an alkoxy, thioalkyl or aminoalkyl, the subscript refers to the number of carbon atoms that the group may contain in addition to heteroatoms. Thus, for example, monovalent $C_{1-2}$aminoalkyl includes the groups —CH$_2$—NH$_2$, —NH—CH$_3$, —(CH$_2$)$_2$—NH$_2$, —NH—CH$_2$—CH$_3$, —CH$_2$—NH$_2$—CH$_3$, and —N—(CH$_2$)$_2$ A lower aminoalkyl comprises an aminoalkyl having one to four carbon atoms.

The alkoxy, thioalkyl, or aminoalkyl groups may be monovalent or bivalent. By "monovalent" it is meant that the group has a valency (i.e., power to combine with another group), of one, and by "bivalent" it is meant that the group has a valency of two. Thus, for example, a monovalent alkoxy includes groups such as —O—$C_{1-12}$alkyl, —$C_{1-6}$alkylene-O—$C_{1-6}$alkyl, —$C_{1-4}$alkylene-O—$C_{1-4}$alkylene-O—$C_{1-4}$alkyl, whereas a bivalent alkoxy includes groups such as —O—$C_{1-12}$alkylene-, —$C_{1-6}$alkylene-O—$C_{1-6}$alkylene-, —$C_{1-4}$alkylene-O—$C_{1-4}$alkylene-O—$C_{1-4}$alkylene-, and so forth.

The term "acyl" refers to a carbonyl group

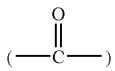

linked to an organic radical including an alkyl, alkenyl, alkynyl, aminoalkyl, substituted alkyl, substituted alkenyl, or substituted alkynyl, as defined above. The organic radical to which the carbonyl group is attached may be monovalent (e.g., —C(=O)-alkyl), or bivalent (e.g., —C(=O)alkylene, etc.)

The term "alkoxycarbonyl" refers to a carboxy or ester group

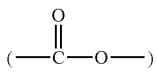

linked to an organic radical including an alkyl, alkenyl, alkynyl, aminoalkyl, substituted alkyl, substituted alkenyl, substituted alkynyl, or substituted aminoalkyl group, as defined above. The organic radical to which the carboxy group is attached may be monovalent (e.g., —CO$_2$-alkyl), or bivalent (e.g., —CO$_2$-alkylene, etc.)

The term "cycloalkyl" refers to fully saturated and partially unsaturated hydrocarbon rings of 3 to 9, preferably 3 to 7 carbon atoms. Accordingly, as herein defined, the term "cycloalkyl" is intended to include introductory chemistry text definitions of a cycloalkenyl group. The term "substituted cycloalkyl" refers to such rings having one, two, or three substituents, preferably one, selected from the group consisting of halo, alkyl, substituted alkyl (e.g., trifluoromethyl), alkenyl, alkynyl, nitro, cyano, amino, oxo, hydroxy, alkoxy, alkylthio, —NH(alkyl), —NH(cycloalkyl), —N(alkyl)$_2$, —NHSO$_2$, —N(alkyl)SO$_2$, —NHSO$_2$(alkyl), —NHSO$_2$(aryl), —N(alkyl)SO$_2$(alkyl), —N(alkyl)SO$_2$(aryl), —SO$_2$(alkyl), —SO$_2$(aryl), —SO$_2$N(aryl)(alkyl), —SO$_2$N(alkyl)$_2$, —CO$_2$H, —C(=O)H, CO$_2$-alkyl, —C(=O)alkyl, —C(=O)NH$_2$, —C(=O)NH(alkyl), —C(=O)NH(cycloalkyl), —C(=O)N(alkyl)$_2$, —NH—CH$_2$—CO$_2$H, —NH—CH(alkyl)-CO$_2$H, —NH—CH$_2$—CO$_2$-alkyl, —NH—CH(alkyl)-CO$_2$-alkyl, keto, =N—OH, =N—O-alkyl, aryl, heteroaryl, heterocyclo, and a five or six membered ketal, i.e. 1,3-dioxolane or 1,3-dioxane.

The term "halo" or "halogen" refers to chloro, bromo, fluoro and iodo.

The term "aryl" refers to phenyl, biphenyl, 1-naphthyl and 2-naphthyl, with phenyl being preferred. The term "aryl" includes such rings having from zero, one, two or three substituents selected from the group consisting of halo, alkyl, substituted alkyl, alkenyl, alkynyl, nitro, cyano, amino, hydroxy, alkoxy, alkylthio, —NH(alkyl), —NH(cycloalkyl), —N(alkyl)$_2$, —NHSO$_2$, —N(alkyl)SO$_2$, —NHSO$_2$(alkyl), —NHSO$_2$(aryl), —N(alkyl)SO$_2$(alkyl), —N(alkyl)SO2(aryl), —SO$_2$(alkyl), —SO$_2$(aryl), —SO$_2$N(aryl)(alkyl), —SO$_2$N(alkyl)$_2$, —CO$_2$H, —C(=O)H, CO$_2$-alkyl, —C(=O)alkyl, —C(=O)NH$_2$, —C(=O)NH(alkyl), —C(=O)NH(cycloalkyl), —C(=O)N(alkyl)$_2$, —NH—CH$_2$—CO$_2$H, —NH—CH(alkyl)-CO$_2$H, —NH—CH$_2$—CO$_2$-alkyl, —NH—CH(alkyl)-CO$_2$-alkyl, phenyl, benzyl, phenylethyl, phenyloxy, phenylthio, cycloalkyl, substituted cycloalkyl, heterocyclo, and heteroaryl.

The term "heterocyclo" refers to substituted and unsubstituted non-aromatic 3- to 7-membered monocyclic groups, 7- to 1-membered bicyclic groups, and 10- to 15-membered tricyclic groups, in which at least one of the rings has at least one heteroatom (O, S or N). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from the group consisting of halo, alkyl, substituted alkyl, alkenyl, alkynyl, nitro, cyano, amino, oxo, hydroxy, alkoxy, alkylthio, —NH(alkyl), —NH(cycloalkyl), —N(alkyl)$_2$, —NHSO$_2$, —N(alkyl)SO$_2$, —NHSO$_2$(alkyl), —NHSO$_2$(aryl), —N(alkyl)SO$_2$(alkyl), —N(alkyl)SO$_2$(aryl), —SO$_2$(alkyl), —SO$_2$(aryl), —SO$_2$N(aryl)(alkyl), —SO$_2$N(alkyl)$_2$, —CO$_2$H, —C(=O)H, CO$_2$-alkyl, —C(=O)alkyl, —C(=O)aryl, —C(=O)NH$_2$, —C(=O)NH(alkyl), —C(=O)NH(cycloalkyl), —C(=O)N(alkyl)$_2$, —NH—CH$_2$—CO$_2$H, —NH—CH$_2$—CO$_2$-alkyl, —NHCH(C$_{1-4}$ alkyl)-CO$_2$H, —NHCH(C$_{1-4}$alkyl)CO$_2$-alkyl, aryl, heteroaryl, heterocyclo, keto, =N—OH, =N—O-alkyl, and a five or six membered ketal, i.e., 1,3-dioxolane or 1,3-dioxane.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl and pyrrolizinyl.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, nitro, cyano, amino, hydroxy, alkoxy, alkylthio, —NH(alkyl), —NH(cycloalkyl), —N(alkyl)$_2$, —NHSO$_2$, —N(alkyl)SO$_2$, —NHSO$_2$(alkyl), —NHSO$_2$(aryl), —N(alkyl)SO$_2$(alkyl), —N(alkyl)SO$_2$(aryl), —SO$_2$(alkyl), —SO$_2$(aryl), —SO$_2$N(aryl)(alkyl), —SO$_2$N(alkyl)$_2$, —CO$_2$H, —C(=O)H, CO$_2$- alkyl, —C(=O)alkyl, —C(=O)NH$_2$, —C(=O)NH(alkyl), —C(=O)NH(cycloalkyl), —C(=O)N(alkyl)$_2$, —NH—CH$_2$—CO$_2$H, —NH—CH(alkyl)-CO$_2$H, —NH—CH$_2$—CO$_2$-alkyl, —NH—CH(alkyl)-CO$_2$—alkyl, phenyl, benzyl, phenylethyl, phenyloxy, phenylthio, cycloalkyl, substituted cycloalkyl, heterocyclo, and heteroaryl.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

Throughout the specification, groups and substituents thereof may be chosen by one skilled in the field to provide stable moieties and compounds.

The compounds of formula (I) form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of formula (I) contains both a basic moiety, such as an amine or a pyridine or imidazole ring, and an acidic moiety, such as a carboxylic acid. Pharmaceutically acceptable (i.e., nontoxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate.

Prodrugs and solvates of the inventive compounds are also contemplated. The term "prodrug" denotes a compound which, upon administration to a subject, undergoes chemical conversion by metabolic or chemical processes to yield a compound of the formula (I), and/or a salt and/or solvate thereof. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkyl-benzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Compounds of the formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization. The inventive compounds may be in the free or hydrate form.

Methods of Preparation

The compounds of the invention may be prepared by the exemplary processes described in the following reaction schemes 1 through 10 along with exemplary reagents and procedures for these reactions. Starting materials are commercially available or can be readily prepared by one skilled in the art, and/or modifications can be made to the methods of Schemes 1 to 10, using known methods.

For all of the schemes, the groups E, Q, B, and C are as described herein for a compound of formula (XI), unless otherwise indicated, and appropriate starting materials may be selected by one skilled in the field. Groups designated R', Z, P', and P'' as well as solvents, temperatures, pressures, and other reaction conditions, may readily be selected as appropriate by one skilled in the art. Appropriate protecting groups ("P") and associated references can be found along with the appropriate deprotecting conditions in Greene, Theodora W.; Wuts, Peter G. M. *Protecting Groups in Organic Synthesis*, 3$^{rd}$ ed.; Wiley & Sons: New York, 1999.

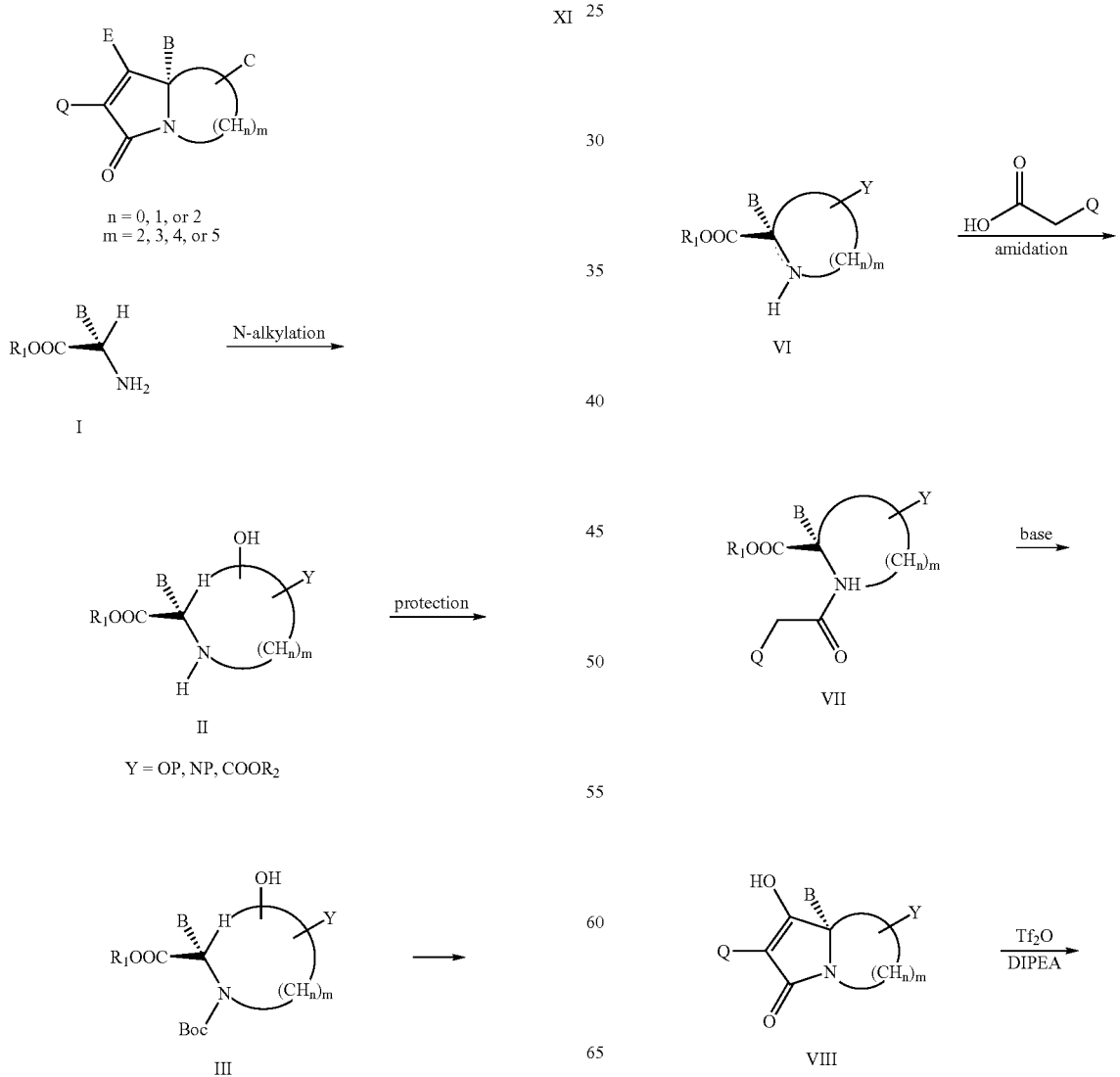

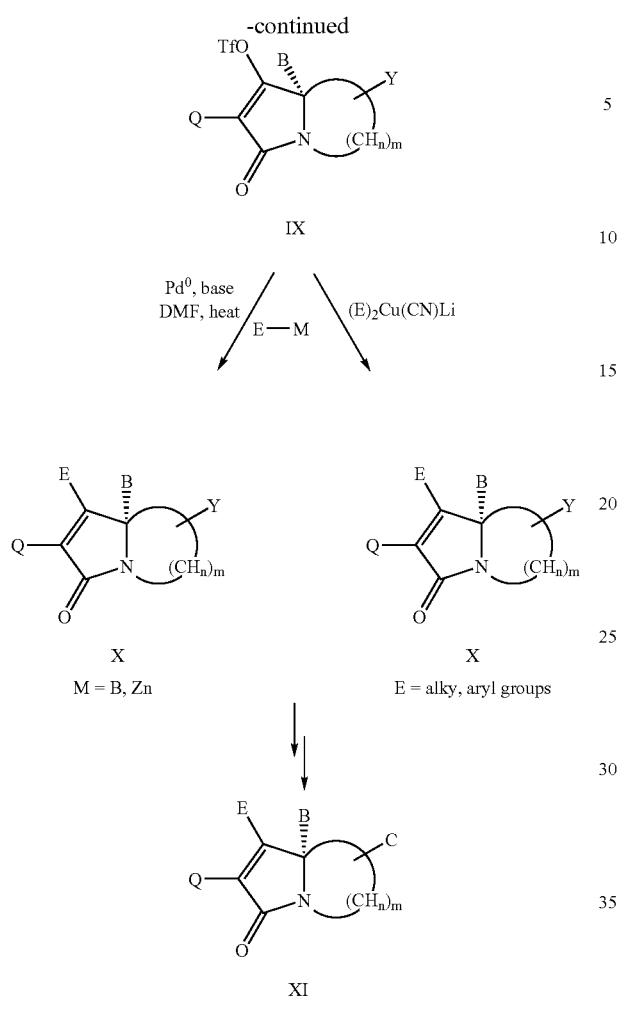

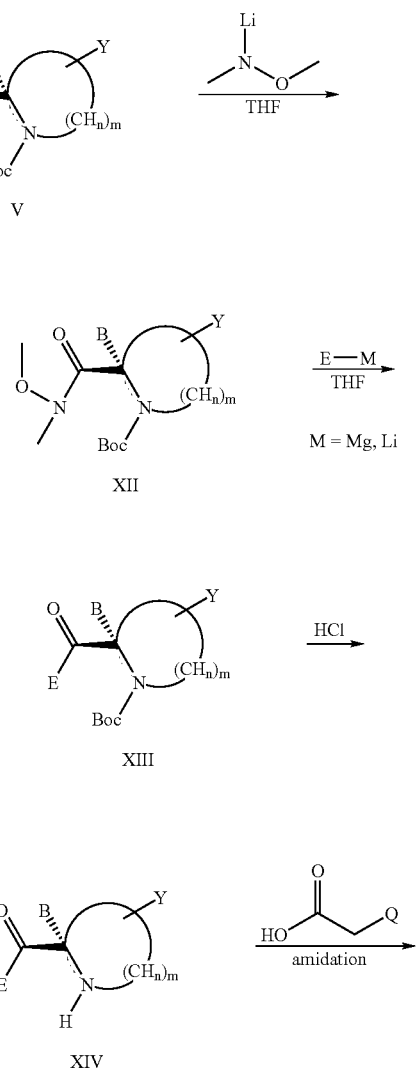

diate towards the generation of XI. Thus VIII can be reacted with a variety of regents to yield XI. The reactions can include metal-catalyzed (e.g. Pd or Ni) coupling organometallic reagents utilizing Stille or Suzuki conditions. Common metals for this transformation include $B(OH)_2$, $SnBu_3$, Zn, Cu, or Mg. Alternatively, cuprate reagents prepared from copper salts and alkyl/aryl Li, alkyl/aryl MgX or alkyl/aryl ZnX organometallic reagents can be used. Replacement of the OTf group with amines can also be facilitated by Pd or Cu mediated amination reactions with aryl or alkyl amines as per Buchwald's cross coupling conditions (Muchi, A. R. and Buchwald, S. L. *Top. Curr. Chem.* 2002, 219, 131-209). Alternatively, functional groups such as a cyano (CN) can be introduced via Pd cross coupling of aryl halides such as Br or I or aryl/enol triflates (OTf) with $Zn(CN)_2$ at elevated temperatures in solvents such as DMF.

As depicted in Scheme 1, Compounds of formula XI can be prepared either as racemic mixtures or in enantiomerically pure form from compounds of formula VI, which can be prepared according to the method of Kawabata et al. (Kawabata et al. *J. Am. Chem. Soc* 125 (2003), 13012-13013). The method can be readily adapted or modified by one skilled in the art. The appropriately substituted α-amino acid ester may be appropriately mono-N-alkylated with an appropriate chain length haloalkyl alcohol and protected as a urethane with a group such as a Boc group. The alcohol functionality is transformed to a halogen, such as a Br or I, and upon treatment with a strong base such as KHMDS, LiHMDS, NaHMDS or LDA in solvents such as DMF or THF at temperatures below −60° C. the cyclic amino acid ester is generated. Under certain conditions, the chiral integrity of the original stereo center is almost completely conserved. Thus, the cyclic amino acid esters can be prepared either as a racemic mixture or in enantiopure forms.

The Boc protecting group of the cyclized amino acid esters can be removed under acidic conditions and converted to appropriate amides of formula VII. When treated with an appropriate base such as LDA, LHMDS or KtOBu bicycles of formula VIII can be isolated. Compound VIII can be converted to the triflate IX which serves as a key interme-

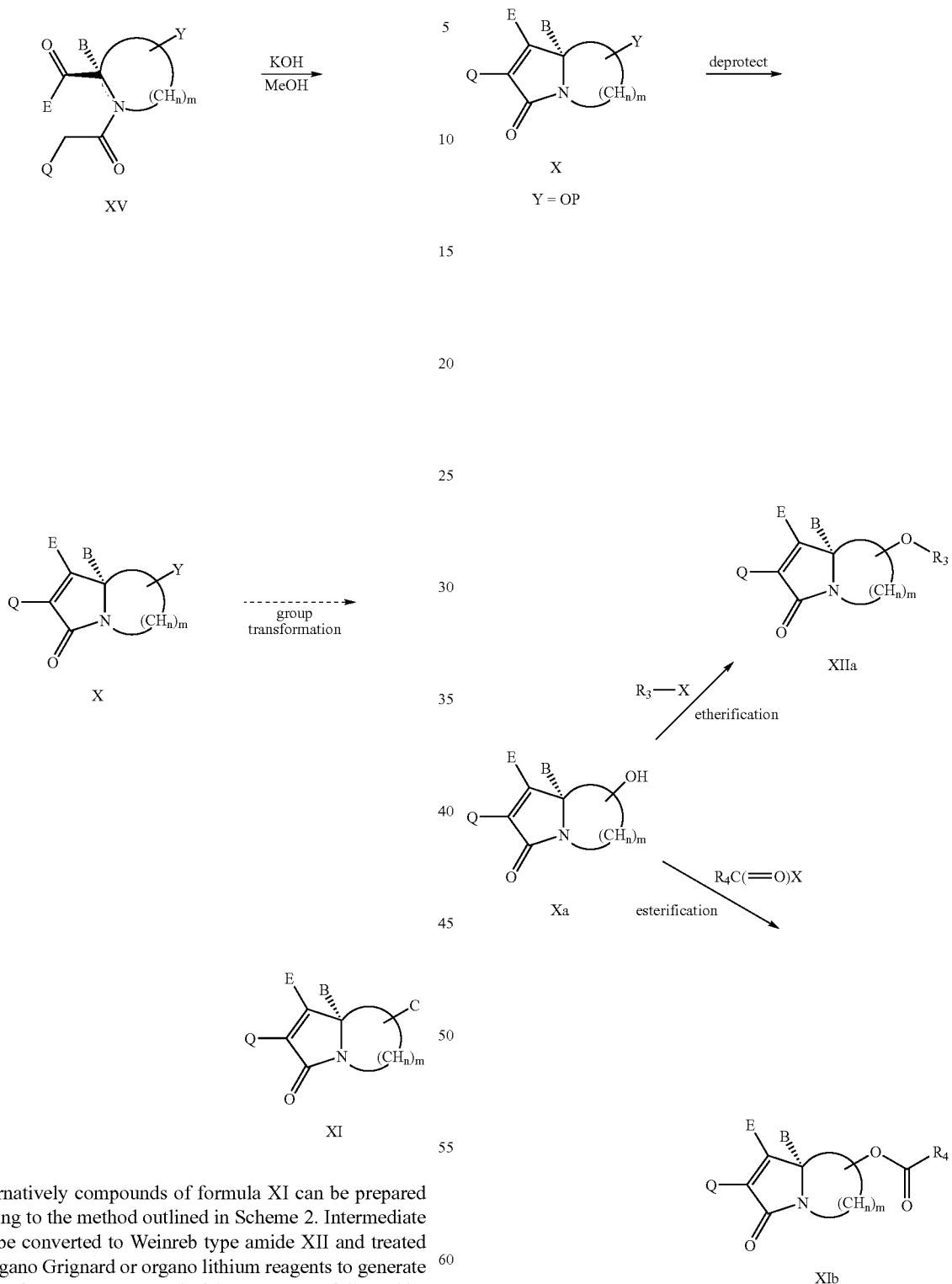

Alternatively compounds of formula XI can be prepared according to the method outlined in Scheme 2. Intermediate V can be converted to Weinreb type amide XII and treated with organo Grignard or organo lithium reagents to generate ketones of type XIII. Removal of the Boc-group followed by amide formation with requisite acetic acid using standard amide forming conditions yields XV. Exposure to a base such as KOH in alcoholic solvent yields the penultimate bicyclic unsaturated lactam X. Transformation of the Y substitutent of X leads final compounds of formula XI.

Additionally, compounds of type Xa where Y is a hydroxyl functionality can be transformed to ethers of type XIa or esters of type XIb using standards modification by those skilled in the field of organic synthesis (Scheme 3).

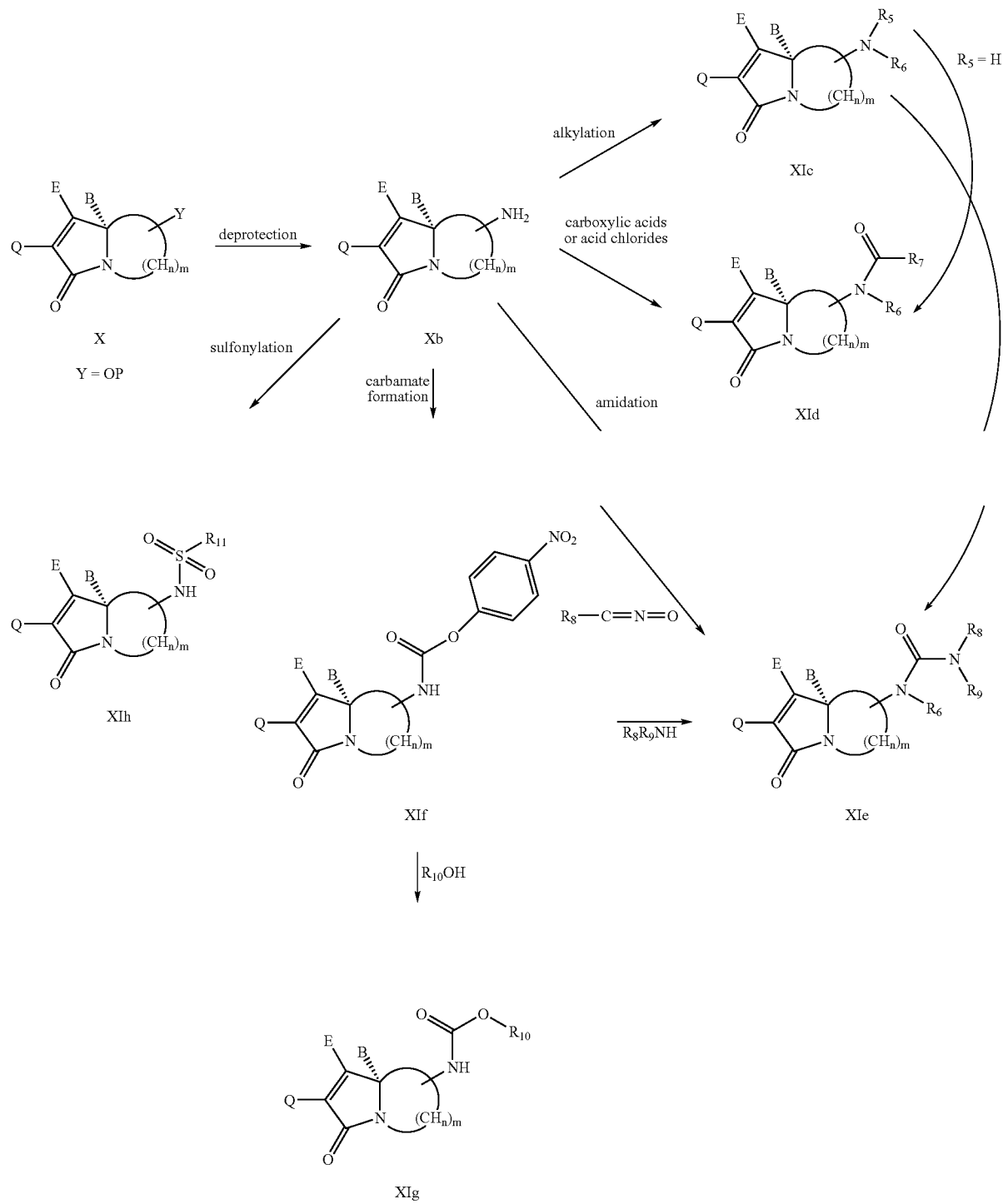

Scheme 4

Compounds of type Xb, where Y is an NH$_2$ group, can be transformed to several different types of functionalities as shown in Scheme 4. Reductive alkylation of Xb with aldehydes or ketones or selective alkylation with alkyl halides results in compounds of type XIc. Reaction of Xb or XIc with carboxylic acid chlorides in the presence of base or carboxylic acids along with standard coupling agents leads to amides of type XId. Urea derivatives of type XIe can also be prepared either starting from Xb via XIf or by reacting directly with isocynates of formula R$_8$=C=N=O. XIc can also serve as a precursor for preparation of XIe. Reaction of XIf with alcohols to give carbamates of type XIg. Sulfonamides of formula XIh can also be prepared by reacting Xb or XIc (R$_5$=H) with sulfonyl chlorides.

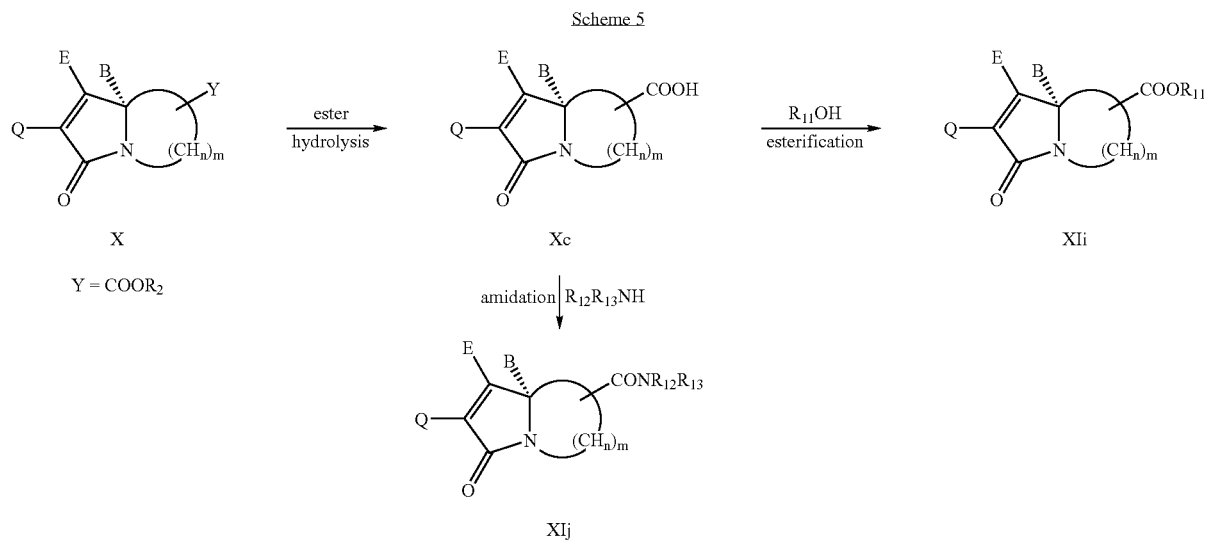
Compounds of formula Xc (Y=COOH), can readily be converted to esters Xii, when reacted with alcohols, and to amides of type XIj, when reacted with primary or secondary amines (Scheme 5).
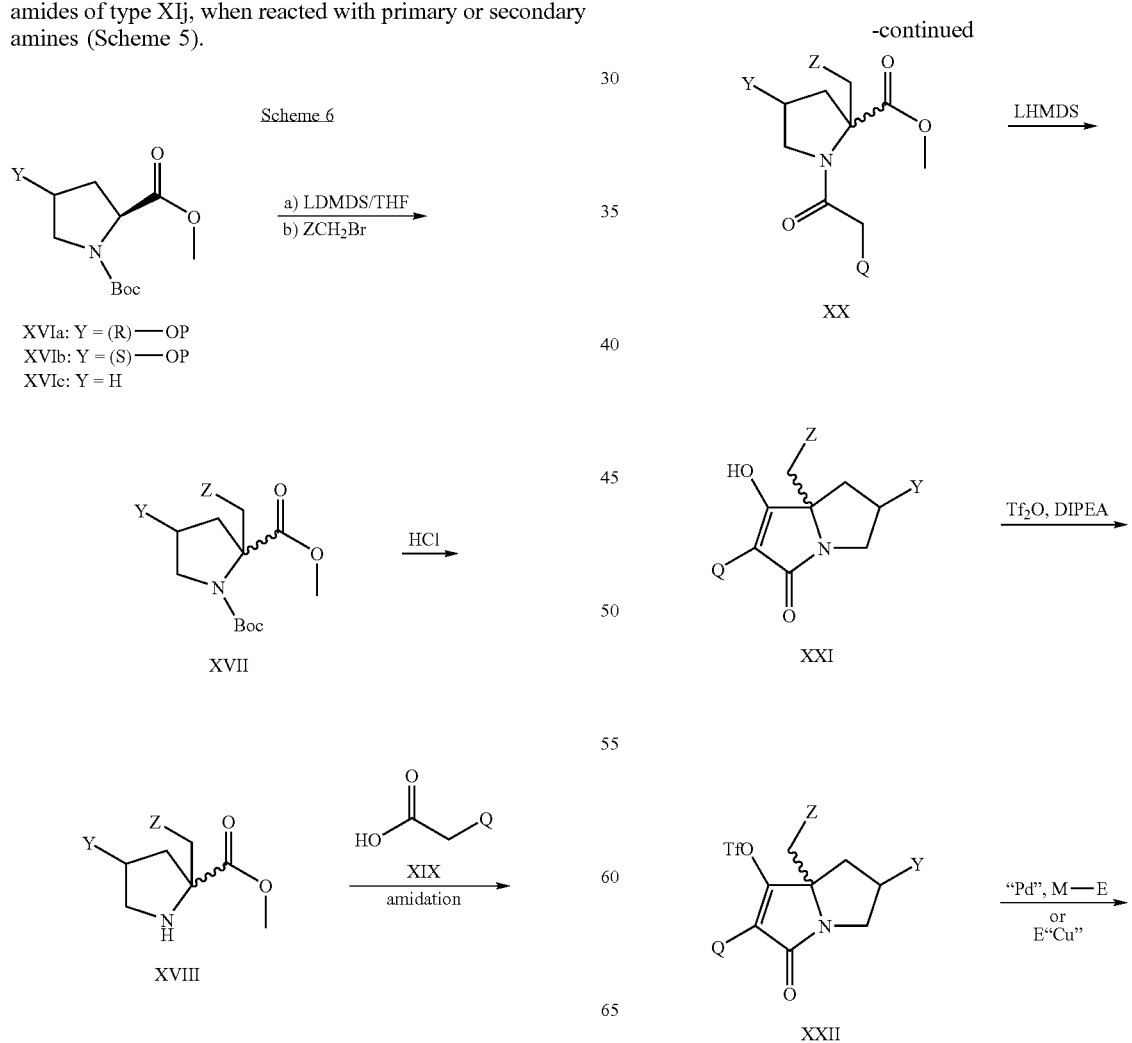

tives of formula XI as described previously. For example, removal of the protecting group generates free OH (Xd), which can be directly functionalized to give XIk. Alternatively, Xd can be converted to an amine compound Xe using techniques familiar to those practicing the art (see Nagumo et al., *Tetrahedron* 58 (2002) 9871-9877). Xe can in turn be converted to compounds of formula XII, similar to those discussed previously in Scheme 4.

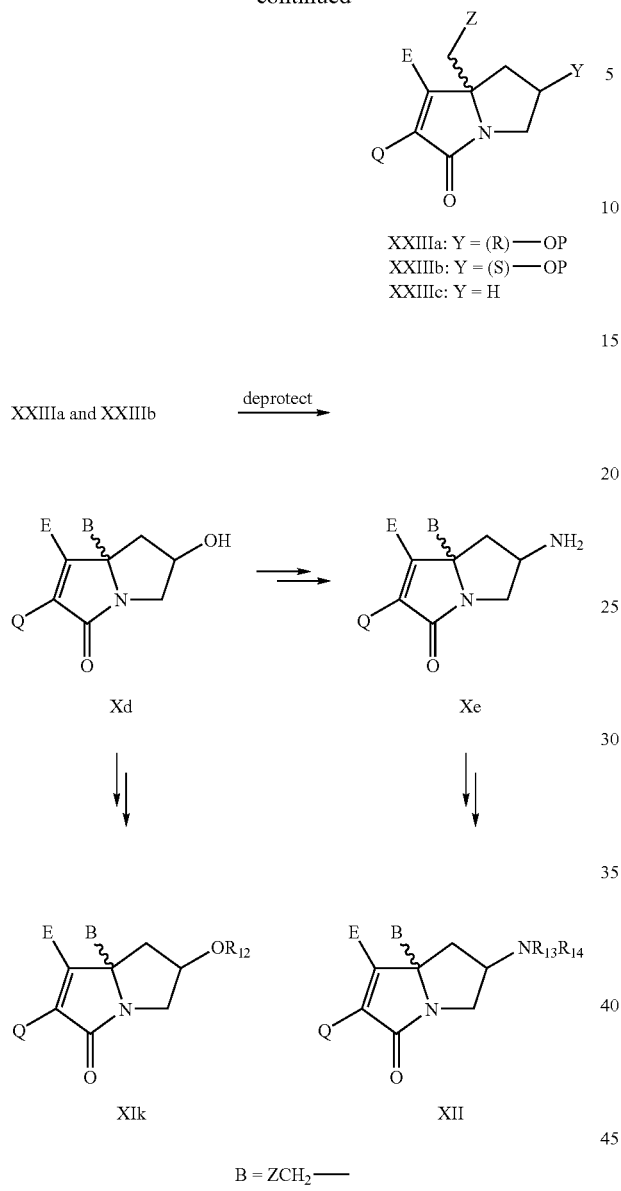

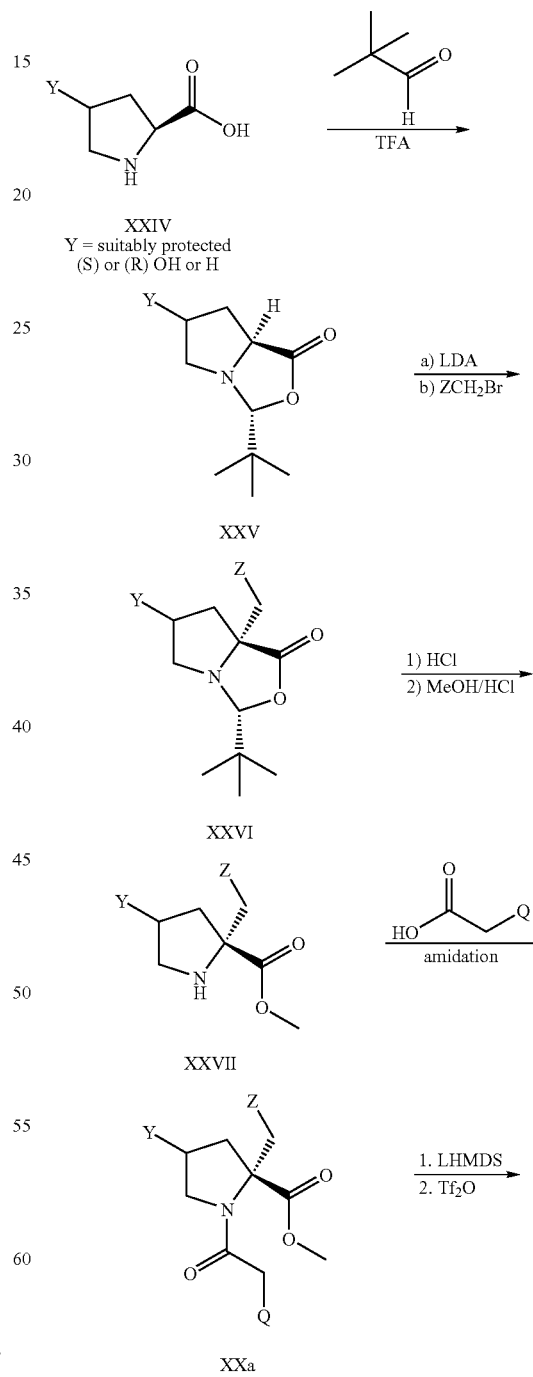

Alternatively, compounds of formula XI where m=3, can be prepared from commercially available materials XVIa-c (Scheme 6). Treatment of XVI with a strong base such as LiHMDS or LDA followed by the addition of alkylating agent (ZCH$_2$—X) leads to XVII (see Nagumo et al. *Tetrahedron Lett.* 40 (1999), 3209-3212). The N-Boc protecting group is readily removed upon exposure to strong acids such as HCl or TFA to yield XVIII. Amide XX is prepared by coupling a carboxylic acids (XIX) with amine XVIII using standard coupling reagents, for example EDCI (1-(3-dimethylaminopropyl)-3-ethylcarbodiimide). Upon treatment with a strong base, such LHMDS or K'OBu, XX is readily converted to the bicyclic lactam XXI. The enolic OH of XXI is converted to a triflate (OTf) (XXII) by treatment with trifluoromethylsulfonic acid anhydride (Tf$_2$O) which serves as a key convenient intermediate for the introduction of substitutent E, as previously discussed.

For compounds of formula XXIII where Y=OP, the Y functionality can be further manipulated to generate deriva-

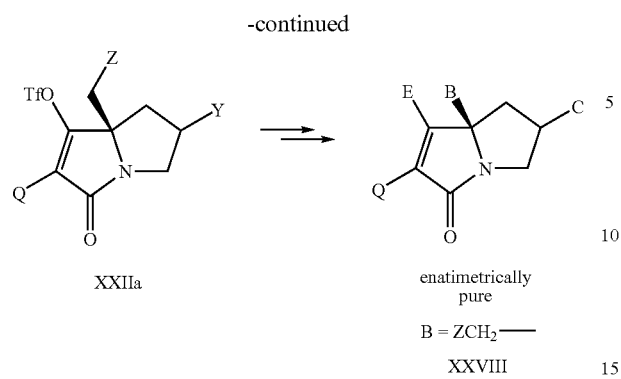

Alternatively, Compounds of formula XXVII can be prepared in optically pure form starting from compounds of formula XXV (Scheme 7) Which is in turn prepared by cyclizing appropriately protected optically pure proline derivatives XXIV with t-butanal in the presence of TFA. See Weber et al., *Helvetica Chimica acta*, 68 (1985),158; and Seebach et al., *J. Am. Chem. Soc.*, Vol. 105(16) (1983), 5390-5398. The alkylation of the oxazolidinone of formula XXV with BrCH$_2$-Z in the presence of LDA in THF to yield compounds of type XXVI. Compounds of type XXVI can be converted to enantiopure compounds of the type XXVIII via the triflate XXIIa as described earlier.

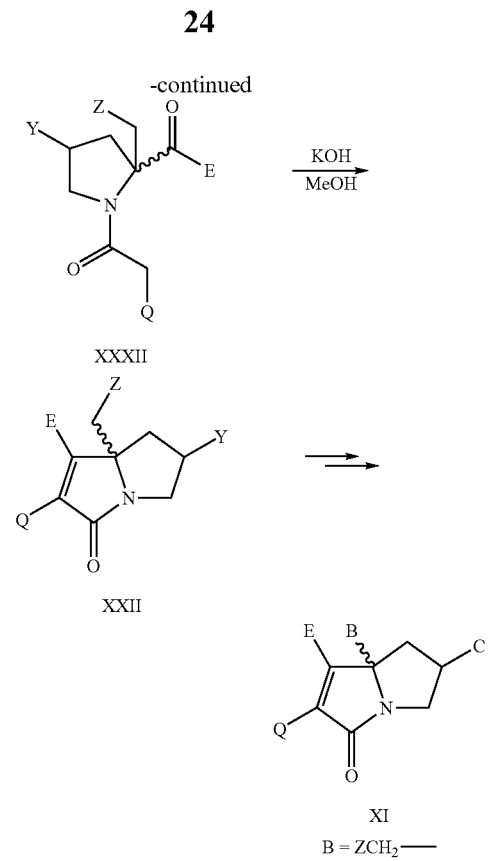

Compounds of formula XI, where n=3, can also can be prepared according to the method outlined in Scheme 8. Intermediate XVII can be converted to Weinreb type amide XXIX by treatment with lithium or Magnesium anions of methoxymethyamine. Subsequent treatment with an organo Grignard or organo lithium reagent generates ketones of type XXX. Removal of the Boc-group followed by amide formation with requisite acetic acids using standard amide forming conditions with EDCI yields XXXII. Exposure to a base such as KOH in alcoholic solvent yields the penultimate bicyclic unsaturated lactam XXII. Transformation of the Y substitutent of XXII leads final compounds of formula XI, similar to those described in Scheme 6.

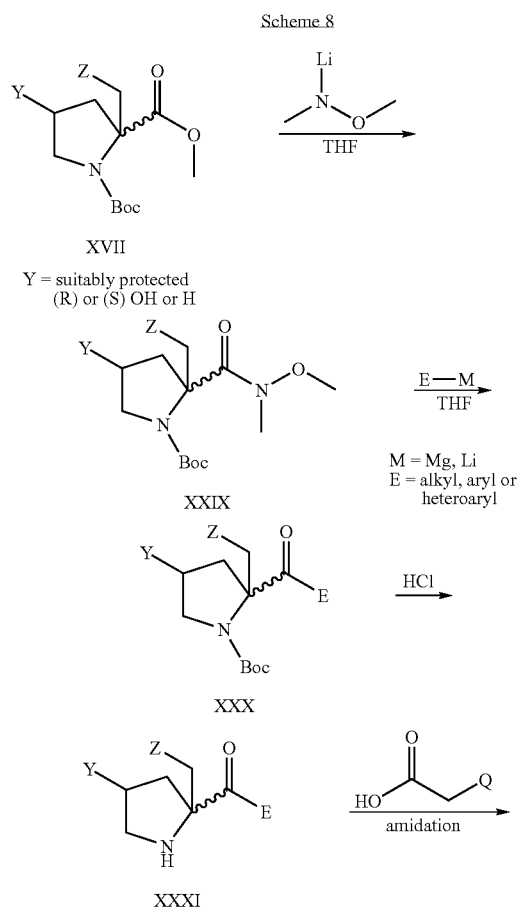

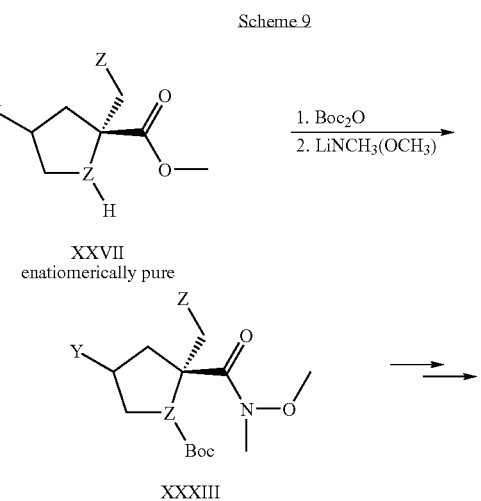

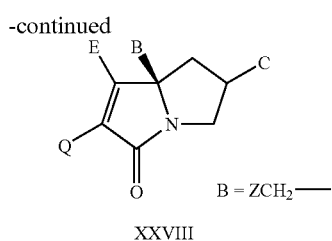

XXVIII

The enantiomerically pure derivatives XXVIII can be prepared using the procedure outlined in Scheme 8 but starting with optically pure compounds of formula XXVII (Scheme 9).

a solvent such as THF with a strong base such as LDA, potassium, lithium or sodium bis(trimethylsilyl)amide (KHMDS, LiHMDS, or NaHMDS) generates an enolate which can be reacted with an electrophile $ZCH_2X$ to give XXXV. Deprotection of the N-1 nitrogen followed by coupling with phenyl acetic acids under amide-forming conditions (EDCI, DIPEA) in a solvent such as DMF yields the amide XXXVII. Treatment of XXXVII with a strong base such LiHMDS or K'OBu in THF results in the isolation of bicycle XXXVIII, which in turn can be converted to the vinyl triflate XXXIX using previously described conditions. Compounds of formula XXXIX can then be converted to compounds of type XXXX using metal-catalyzed (e.g. Pd or Ni) coupling of organometallic reagents as previously described. Alternatively, cuprate reagents prepared from copper salts and

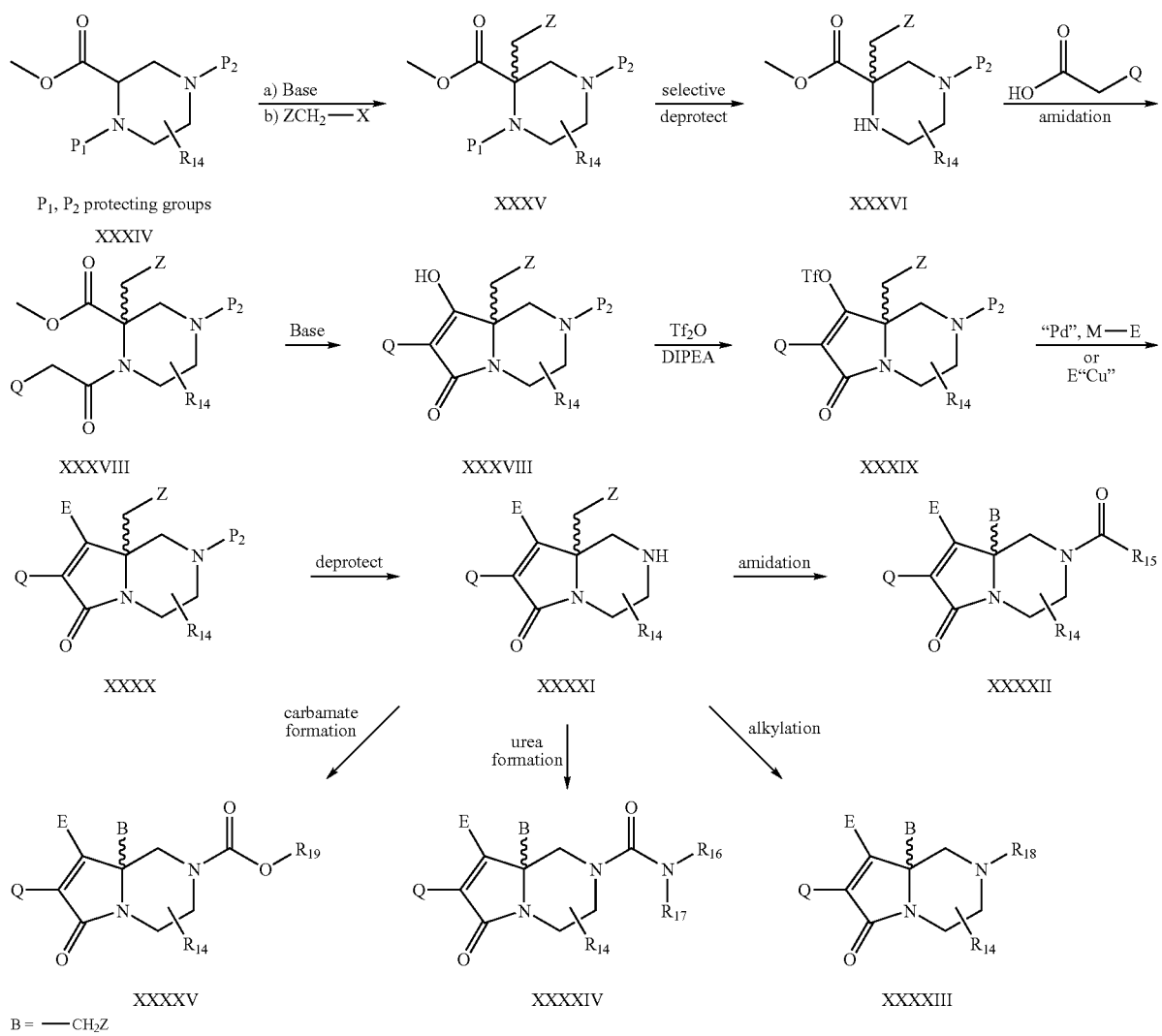

In addition, piperazine-containing compounds of formulae XXXXII-XXXXIV can be synthesized from a differentially bis protected piperazine XXXIV as shown in Scheme 10. See Hu et al. *Bioorg. Med. Chem. Lett.* 9, (1999), 1121-1126. Treating XXXIV at low temperature (−78° C.) in alkyl lithium or magnesium can also be used to introduce fragment E. Deprotection of N-2 followed by re-functionallization with various reagents capable of reacting with NH of XXXXI yields amides XXXXII, amines XXXXIII, ureas XXXXIV, and carbamates XXXXV.

Preferred Compounds

In addition to the preferred embodiments referred to in the Preferred compounds of the present invention are those compounds within the scope of formula (Ia) (above), or a pharmaceutically-acceptable salt, enantiomer or diastereomer thereof, wherein:

A is a saturated 5- or 6-membered heterocyclo ring;

$R^1$ is $(CH_2)_r$-Z, wherein Z is phenyl substituted by zero to three $R^{10}$;

$R^2$ is phenyl substituted with zero to two $R^{11}$ or pyridyl substituted zero to two $R^{11}$; and $R^3$ is (i) attached to any available carbon or nitrogen atom of ring A and at each occurrence is selected independently of other $R^3$ from halogen, alkyl, substituted alkyl, alkenyl, alkynyl, nitro, cyano, oxo, $OR^8$, $NR^8R^9$, $CO_2R^8$, $C(=O)R^8$, $C(=O)NR^8R^9$, $NR^8C(=O)R^9$, $NR^8C(=O)OR^9$, —OC(=O)$R^8$, —OC(=O)$NR^8R^9$, $S(O)_qR^8$, $NR^8SO_2R^9$, $SO_2NR^8R^9$, aryl, heteroaryl, heterocyclo, cycloalkyl, and substituted cycloalkyl; and $R^{10}$ and $R^{11}$ at each occurrence are selected independently from halogen, alkyl, substituted alkyl, alkenyl, alkynyl, nitro, cyano, $OR^{12}$, $NR^{12}R^{13}$, $CO_2R^{12}$, and $C(=O)R^{12}$.

Also preferred are compounds within the scope of formula (Ia) having the formula (Ib):

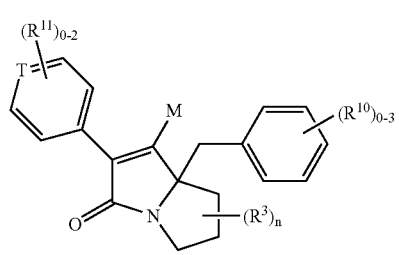

(Ib)

or a pharmaceutically-acceptable salt, prodrug, enantiomer, or diastereomer thereof, wherein T is selected from CH or N.

Preferred compounds within the scope of formula (Ib) are those in which M is hydrogen, halogen, nitro, cyano, $C_1$-$C_4$alkyl, trifluoromethyl, —O($C_1$-$C_4$alkyl), $NR^6R^7$, $CO_2R^6$, $C(=O)R^6$, $C(=O)NR^6R^7$, $S(O)_qR^6$, or $SO_2NR^6R^7$ (especially $C_1$-$C_4$alkyl); $R^3$ is selected from halogen, $C_1$-$C_4$alkyl, trifluoromethyl, alkenyl, alkynyl, nitro, cyano, $OR^8$, $NR^8R^9$, $CO_2R^8$, $C(=O)R^8$, $C(=O)NR^8R^9$, $NR^8C(=O)R^9$, $NR^8C(=O)OR^9$, —OC(=O)$R^8$, —OC(=O)$NR^8R^9$, $S(O)_qR^8$, $NR^8SO_2R^9$, $SO_2NR^8R^9$, aryl, heteroaryl, heterocyclo, cycloalkyl and substituted cycloalkyl; and n is 0 or 1.

More preferred are compounds within the scope of formula (Ib), or a pharmaceutically-acceptable salt, enantiomer or diastereomer thereof, in which T is N.

Alternatively more preferred compounds within the scope of formula (Ib) are those in which T is CH.

Other preferred compounds within the scope of formula (Ib) have the formula (Ic):

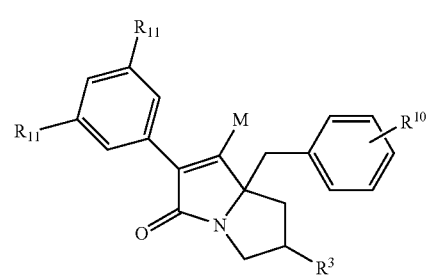

(Ic)

or a pharmaceutically-acceptable salt, enantiomer, or diastereomer, thereof.

Preferred compounds within the scope of formula (Ic), or a pharmaceutically-acceptable salt, enantiomer, or diastereomer, thereof, are those in which M is $C_1$-$C_4$alkyl or substituted $C_1$-$C_4$alkyl; $R^3$ is selected from amino, chloro, fluoro, bromo, cyano, nitro, methyl, ethyl, i-propyl, n-propyl, hydroxy, methoxy, aryloxy, —OC(=O)aryl, cyclopropyl, cyclobutyl, cyano, and nitro (especially where $R^3$ is hydroxy or —OC(=O)phenyl); $R^{10}$ is chloro, fluoro, bromo, alkyl, trifluoromethyl, nitro, cyano, hydroxy, or alkoxy (especially where $R^{10}$ is halogen or cyano); and $R^{11}$ independently at each occurrence is chloro, fluoro, bromo, alkyl, trifluoromethyl, nitro, cyano, hydroxy, alkoxy, phenyloxy, —$CO_2H$, —C(=O)H, amino, NH(alkyl), N(alkyl)$_2$, $CO_2$alkyl, C(=O)alkyl, or alkylthio.

More preferred compounds within the scope of formula (Ic), or a pharmaceutically-acceptable salt, enantiomer, or diastereomer. thereof, are those in which M is methyl, ethyl, propyl, cyclopropyl, or $CF_3$; $R^3$ is hydroxy or —OC(=O)phenyl; $R^{10}$ is chloro, fluoro, bromo, or cyano (especially bromo or cyano); and $R^{11}$ independently at each occurrence is chloro, fluoro, or bromo (especially where each $R^{11}$ is chloro).

Even more preferred are compounds in which M is ethyl, or cyclopropyl.

Utility

The compounds and compositions of this invention are antagonists of LFA-1. Thus, they are useful in treating various inflammatory diseases and disorders associated with the action of LFA-1, Mac-1, and/or ICAMs, particularly LFA-1:ICAM-1. The term "Leukointegrin/ICAM-associated condition" is used herein for ease of reference to refer to those diseases or disorders that are associated with the action or levels of LFA-1. As used herein the term "treating" includes prophylactic and therapeutic uses and refers to the alleviation of symptoms of a particular disorder in a patient, the improvement of an ascertainable measurement associated with a particular disorder, or the prevention of a particular immune response (such as transplant rejection). The term "patient" refers to a mammal, preferably a human.

The inventive compounds and compositions are useful for treating a wide range of conditions, as the action of LFA-1 and/or ICAMs is associated with the influx of leukocytes in almost every system, including the skin, peritoneum, synovium, lung, kidney and heart. The inventive compounds may be used to treat conditions resulting from a response of the specific immune system in a patient or the nonspecific immune system. Such conditions include, for example, graft vs host reactions and transplant rejection (e.g., kidney, liver, heart, lung, pancreas, bone marrow, cornea, small bowel, skin allografts, skin homografts and heterografts, etc.); psoriasis, organ-tissue autoimmune diseases (e.g., Raynaud's syndrome), autoimmune thyroiditis, dermatitis, multiple sclerosis, rheumatoid arthritis, insulin dependent diabetes mellitus, uveitis, inflammatory bowel disease including Crohn's disease and ulcerative colitis and systemic lupus erythematosus, adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infraction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome, pulmonary fibrosis, atherosclerosis, meningitis, encephalitis, experimental autoimmune encephalomyelitis, Sjorgen's syndrome, and juvenile onset diabetes. The compounds of the present invention are especially suitable for the treatment of acute or chronic transplant rejection, rheumatoid arthritis, osteoarthritis, diabetes, asthma, inflammatory bowel disease, psoriasis, and chronic obstructive pulmonary disease.

The compounds of the present invention also may be used to treat allergic conditions such as eczema and asthma or as an adjunct to minimize toxicity with cytokine therapy in the treatment of cancers. In view of their inhibition activity, the compounds may be used to treat inflammatory conditions that involve the infiltration of T-cells and chronic inflammatory responses, hypersensitivity reactions, such as skin hypersensitivity reactions (including poison ivy and poison oak), immune responses associated with delayed hypersensitivity mediated by cytokines and T-lymphocytes, and metastases.

The compounds of this invention further have utility in treating hypogonadism, frailty, osteoporosis, sexual dysfunction, wasting, such as wasting syndromes associated with cancer and AIDS, and anemia. The compounds further have utility in treating cancers, including but not limited to cancers of the breast, brain, skin, ovary, endometrium, bladder, prostate, lung, colon, lymphatic system, liver and kidney. The compounds of the present invention are useful for conditions such as hirsutism, Alzheimer's disease, non-insulin dependent diabetes mellitus, acne, seborrhea, alopecia, fibroids, hyperpilosity, cachexia, polycystic ovarian syndrome, anorexia, contraception, drug withdrawal syndrome, pregnancy termination, and benign prostate hypertrophy. The compounds are further useful as antiangiogenic agents.

When used as anti-inflammatory agents, the compounds may be administered prior to the onset of, at, or after the initiation of inflammation. When used prophylactically, the compounds are preferably provided in advance of any inflammatory response or symptom (for example, prior to, at, or shortly after the time of an organ or tissue transplant but in advance of any symptoms or organ rejection). Administration of the compounds may prevent or attenuate inflammatory responses or symptoms.

The present invention thus provides methods for treating such conditions as those listed above, comprising administering to a subject in need thereof an effective amount of at least one compound of formula (I) or a salt thereof. Other therapeutic agents such as those described below may be employed in combination with the compounds of formula (I). In the methods of the present invention, such other therapeutic agent(s) may be administered prior to, simultaneously with, or following the administration of the inventive compounds.

The present invention also provides pharmaceutical compositions capable of treating the Leukointegrin/ICAM-associated conditions and above-described diseases and disorders. The inventive compositions may contain other therapeutic agents and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmnotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a patient of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and the particular condition sought to be treated and its severity. Preferred subjects for treatment include animals, most preferably mammalian species such as humans, and domestic animals such as dogs, cats, horses, and the like, subject to Leukointegrin/ICAM associated conditions and/or subject to any of the above-referenced diseases and disorders.

The inventive compounds and compositions may be employed alone or in combination with each other and/or other suitable therapeutic agents useful in treating Leukointegrin/ICAM-associated conditions and diseases and disorders referenced above. Exemplary of such other therapeutic agents include corticosteroids, cyclosporin, methotrexate, CELLCEPT™ (mycophenolate mofetil), co-stimulation blockades, growth hormones, and growth hormone secretagogues. Additionally, the inventive compounds may be administered either alone or in combination with anti-cancer and cytotoxic agents and treatments useful in treating cancer or other proliferative diseases, for example, where the second drug has the same or different mechanism of action than the present compounds. Examples of classes of anti-cancer and cytotoxic agents useful in combination with the present compounds include but are not limited to: alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids and epipodophyllotoxins; topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. The compounds of the invention may be used in conjunction with radiation therapy.

Representative examples of these classes of anti-cancer and cytotoxic agents that may be used in combination with the inventive compounds include but are not limited to paclitaxel, cisplatin, carboplatin, doxorubicin, carminomycin, daunorubicin, idarubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine, mechlorethamine hydrochloride, cyclophosphamide, chlorambucil, ifosfamide, busulfan, carmustin, lomustine, semustine, streptozocin, thiotepa, dacarbazine, methotrexate, thioguanine, fludarabine, pentastatin, cladribin, cytarabine, bleomycin, mitomycin C, actinomycin D, safracins, saframycins, quinocarcins, discodermolides, vinorelbine, tamoxifen, estramustine, flutamide, buserelin, leuprolide, pteridines, diynes, levamisole, aflacon, interferon, interleukins, aldesleukin, filgrastim, sargramostim, rituximab, BCG, tretinoin, irinotecan, betamethasone, altretamine, and topotecan and any analogs or derivatives thereof.

Examples of anticancer and other cytotoxic agents that may be used in combination with the inventive compounds include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416; and prenyl-protein transferase inhibitors as found in WO 97/30992 and WO 98/54966.

The above other therapeutic agents, when employed in combination with the compounds of the present invention, may be used, for example, in those amounts indicated in the Physicians' Desk Reference (PDR) or as otherwise determined by one of ordinary skill in the art.

The inventive compounds, as represented by those described in the following experimental section, have been tested in cell-cell assays (described below) and demonstrated activity consistent with inhibition of LFA-1 and/or ICAM-1.

Assays

H1-HeLa Adhesion Assay

H1-Hela cells were released from their growth flask using versene (Gibco, Grand Island, N.Y.). Following centrifugation, the cells were resuspended in growth medium: DMEM (Gibco), 10% fetal calf serum (Hyclone, Logan, Utah), 1% Pen-Strep (Gibco), and 1% L-glutamine (Gibco) and plated for growth at 5,000 cells/well in a 96-well plate.

The next day, HSB-2 cells were divided to 2×10$^5$/ml in growth medium: RPMI 1640 (Gibco), 10% FCS, 1% Pen-Strep, and 1% L-glutamine. The next day (day #3), the cells were centrifuged at 534×G for 8 minutes, washed, and resuspended in HBSS at 5×10$^7$/ml. Calcein-AM, 10 µM (Molecular Probes, Eugene, Oreg.) and 100 nM phorbol myristate acetate (SIGMA, St. Louis, Mo.) were added to the labeling and activation mix. Following incubation at 37° C. for 30 minutes, ten ml of HBSS was added and the cells centrifuged as above. The cell pellet was then resuspended and counted.

While the HSB-2 cells were labeling, the medium was aspirated from the H1-HeLa cells and the plates washed once with HBSS, followed by the addition of 50 µl of HBSS. An additional 50 µl of HBSS containing compound solution, DMSO, or anti-CD18 antibody was then added to each well. To the H1-HeLa cells were added 200,000 HSB-2 cells/well in 100 µl, followed by incubation in the dark for 30 minutes. The wells were then washed three times to remove the unbound cells. A fluorescence plate reader was then used to determine the number of bound HSB-2 cells. The percent inhibition due to the compound was calculated using the vehicle control as 0% inhibition and the antibody blocked adhesion as 100% inhibition.

HUVEC Adhesion Assay

On day 1, human umbilical vein endothelial cells (HUVEC) (passage 3, Clonetics, San Diego, Calif.) were placed into a T-75 flask containing EGM bulletkit media (Clonetics) for growth.

When the HUVEC were 90% confluent (typically day 4), 96-well tissue culture plates were coated with 100 µl/well of 2.5 µg/ml mouse Type IV collagen (Gibco) diluted in 0.1 M acetic acid. Following incubation for at least three hours, the collagen was removed and the plate washed three times with HBSS (Gibco). The HUVEC flask was trypsinized, and HUVEC were plated on the collagen coated wells at 1250 cells/200 µl/well for use four days later. Twenty hours prior to use, the medium was removed and cells were stimulated with 200 µl of 1 µg/ml lipopolysaccharide (LPS, Sigma, St. Louis, Mo.) in EGM. When the cells were 90% confluent (typically day 8), the LPS-containing medium was removed, the wells were washed with HBSS, and 50 µl of HBSS was added to the wells. An additional 50 µl containing compound solution, DMSO or blocking anti-CD18 was then added to each well.

On day 7, HSB-2 cells were then divided to 2×10$^5$/ml in RPMI 1640 (Gibco), 10% FCS (Hyclone, Logan, Utah), 1% Pen-Strep (Gibco), and 1% L-glutamine (Gibco). The following day, the cells were centrifuged at 534×G for 8 minutes, washed, and resuspended in HBSS at 5×10$^7$/ml. For activation and labeling, calcein-AM, 10 µM (Molecular Probes, Eugene, Oreg.) and 100 nM phorbol myristate acetate (Sigma, St. Louis, Mo.) were added and the cells incubated at 37° C. for 30 minutes. Following the addition of ten ml of HBSS, the cells were centrifuged, resuspended, and counted.

To the HUVEC cells were added 200,000 labeled and activated HSB-2 cells/well in 100 µl, followed by incubation in the dark for 30 minutes. To remove unbound cells, the wells were washed three times with HBSS. A fluorescence plate reader was used to determine the number of HSB-2 cells bound. The percent inhibition due to the compound was calculated with the vehicle control set at 0% inhibition and the antibody-blocked adhesion set at 100% inhibition.

The following Examples illustrate embodiments of the inventive compounds and starting materials, and are not intended to limit the scope of the claims.

EXAMPLES

For ease of reference, the following abbreviations are used herein:
aq.=aqueous
BOC=tert-butoxycarbonyl
Bu=butyl
c=concentration
° C.=degrees Centigrade
CDCl$_3$=chloroform-d
CD$_3$OD=methanol-d$_4$
CH$_2$Cl$_2$=dichloromethane
d=day(s) or doublet
DIAD=diisopropylazodicarboxylate
DMAP=4-dimethylaminopyridine
DMF=dimethylformamide
DMSO=dimethylsulfoxide
EDC=3-ethyl-3'-(dimethylamino)propylcarbodiimide hydrochloride
Et=ethyl
Et$_3$N=triethylamine
Et$_2$O=diethyl ether
EtOH=ethanol
g=gram(s)
h=hour(s)
HCl=hydrochloric acid
H$_2$O=water
HPLC=high performance liquid chromatography
H$_2$SO$_4$=sulfuric acid
Hz=hertz
iPr=isopropyl
iPr$_2$NEt (DIEA)=diisopropylethylamine
KHMDS=potassium bis(trimethylsilyl)amide
KOH=potassium hydroxide
L=liter(s)
LC/MS=high performance liquid chromatography/mass spectrometry
LiHMDS=lithium bis(trimethylsilyl)amide
LiOH=lithium hydroxide
M=molar
Me=methyl
MeOH=methanol
mg=milligram(s)
MHz=megahertz
µL=microliter(s)
min=minute(s)
mL=milliliter(s)
mmol=millimole(s)
MS or Mass Spec=mass spectrometry
m/z=mass to charge ratio
N$_2$=nitrogen
NaHCO$_3$=sodium bicarbonate
NaHMDS=sodium bis(trimethylsilyl)amide
NaOH=sodium hydroxide
Na$_2$SO$_4$=sodium sulfate
nBuLi=n-butyllithium
NEt$_3$=triethylamine
NH$_4$OH=ammonium hydroxide
NMP=N-methylpyrrolidinone
NMR=nuclear magnetic resonance
Ph=phenyl
Ph$_3$P=triphenylphosphine
(Ph$_3$P)$_4$Pd=tetrakistriphenylphosphine palladium RT=room temperature
sat or sat'd=saturated
TBDMS=tert-butyldimethylsilyl
tBu=tertiary butyl
TFA=trifluoroacetic acid
THF=tetrahydrofuran
TLC=thin layer chromatography
UV=ultraviolet HPLC retention times listed throughout the Examples below were measured under four sets of conditions as described below:

HPLC Column Conditions #1.
Column: Phenom-Prime S5 C18 4.6×30 mm.
Solvents: Solvent A (10% MeOH-90% H2P-0.1% TFA), Solvent B (90% MeOH-10% H2O-0.1% TFA),
Gradient: start % B=0, final % B=100; gradient time 2 min, hold at 100% B for 1 min., flow rate 5 ml/min.

HPLC Column Condition #2.
Column: Phenom-Prime S5 C18 4.6×30 mm.
Solvents: Solvent A (10% MeOH-90% H2O-0.1% TFA), Solvent B (90% MeOH-10% H2O-0.1% TFA),
Gradient: start % B=0, final % B=100; gradient time 4 min, hold at 100% B for 1 min., flow rate=4 ml/min.

HPLC Column Condition #3
Column: YMC-ODS 3.0×50 mm.
Solvents: Solvent A (10% MeOH-90% H2O-0.1% TFA), Solvent B (90% MeOH-10% H2O-0.1% TFA),
Gradient: start % B=0, final % B=100; gradient time 4 min, hold at 100% B for 1 min., flow rate=4 ml/min.

HPLC Column Condition #4.
Column: Chiralcel OD NP 10 μm 4.6×250 mm SN OD00CE-DD049
Solvents: Solvent A=Heptane; Solvent B=EtOH/MeOH (1/1).
Isocratic 15% B/90% A; flow rate=1 ml/min The following procedures exemplify the preparation of intermediates referred to in the Examples.

Preparation of (2) (infra)

Trans-4-hdroxy-L-proline (1) (25 mmol) and imidazole (55 mmol) were suspended in DMF (50 mL) and treated with tert-butyl(dimethyl)silyl chloride (51 mmol). The reaction was stirred for 20 h, poured into water (100 ML) and extracted with diethyl ether ($Et_2O$), 4×50 mL. The organic extracts were combined was washed with 1N HCl aq. (3×30 mL), water (1×50 mL), Sat. aqueous NaHCO3 solution (1×30 mL) and Sat. aq. NaCl solution (1×30 mL). The organic layer was isolated, dried ($MgSO_4$) and solvent removed in vacuo to give pure 1-tert-butyl 2-methyl (2S,4R)-4-{[tert-butyl(dimethyl)silyl]oxy}pyrrolidine-1,2-dicarboxylate (2) as an oil (90%), LCMS (m/z) 261((—C(O)C($CH_3$)).

Preparations of (4)-(7) (infra)

In a three neck flask was suspended appropriate N-Boc Proline methyl ester 2 (1-tert-butyl 2-methyl (2S,4R)-4-{[tert-butyl(dimethyl)silyl]oxy}pyrrolidine-1,2-dicarboxylate) or 3 (1-tert-butyl 2-methyl (2S)-proline-1,2-dicarboxylate) (10 mmol) in anhydrous THF (25 mL) under a nitrogen atmosphere and cooled to −78° C. A solution of LiHMDS (1 Molar in THF, 15 mL, 15 mmol) was added drop wise over 5 min. The reaction was allowed to stir for 30 min after which the appropriate benzyl bromide, 4-bromobenzyl or 4-cyanobenzyl bromide, (12 mmol) was added in small portions over 10 min. The reaction was kept at −78° C. for 2 h and allowed to gradually come to room temperature over −5 h and stirred for an additional 10 h at rt. The reaction mixture was poured into water (100 mL), acidified to pH 1-2 with aqeuous 1N HCl and extracted with diethyl ether (4×50 mL). The combined ether layers were washed with water (50 mL), sat. aq. $NaHCO_3$ solution (50 mL) and sat. aq. NaCl solution (50 mL). The organic layer was dried ($MgSO_4$) and solvent removed in vacuo. The resulting products were purified using silica gel chromatography with EtOAc/Heptane (10/90 to 25/75) give the coeluting products (1-tert-butyl 2-methyl (4R)-2-(4-bromobenzyl)4-{[tert-butyl(dimethyl)silyl]oxy}pyrrolidine-1,2-dicarboxylate (4) (85%), LCMS, (m/z) 552/554 (M++H); 1-tert-butyl 2-methyl (4R)-4-{[tert-butyl(dimethyl)silyl]oxy}-2-(4-cyanobenzyl)pyrrolidine-1,2-dicarboxylate (5) (30-35%), LCMS (m/z, $Na^+$ adduct) 398 ($M^+$-$CO_2$($CH_3$)$_3$); 1-tert-butyl 2-methyl 2-(4-bromobenzyl)pyrrolidine-1,2-dicarboxylate (6) (>90%), LCMS, (m/z) 420/422 ($M^+$+Na); 1-tert-butyl 2-methyl 2-(4-cyanobenzyl)pyrrolidine-1,2-dicarboxylate (7) (35%), 345 ($M^+$+H).

Preparations of (8)-(9) (infra)

A suspension of N-(methoxy)methylaamine hydrochloride (1.17 g, 15 mmol) in anhydrous THF (40 mL), under a nitrogen atmosphere, was cooled to −10° C. and treated with n-BuLi (18.75mL, 30 mmol, 1.6 M in hexanes) and allowed to stir for 30 min. A solution of the appropriate N-Boc Proline methyl ester 1-tert-butyl 2-methyl (4R)-2-(4-bromobenzyl)-4-{[tert-butyl(dimethyl)silyl]oxy}pyrrolidine-1,2-dicarboxylate (4)or 1-tert-butyl 2-methyl 2-(4-bromobenzyl)pyrrolidine-1,2-dicarboxylate (6) (10 mmol) in THF (25 mL) was added drop wise to the reaction via cannula. The reaction was warmed to rt. and stirred for 20 h, poured into water (50 mL), acidified to pH 2 with 1N aqueous HCl and extracted with $Et_2O$ (4×30 mL). The extracts were combined, washed with water (25 mL), sat. aqueous $NaHCO_3$ solution (25mL), sat. aqueous NaCl solution (25 mL) and dried ($MgSO_4$). Solvent was removed in vacuo and the products (8), (9) were used as such in the subsequent reaction without purification. tert-butyl (4R)-2-(4-bromobenzyl)-4-{[tert-butyl(dimethyl)silyl]oxy}-2-{[methoxy (methyl)amino]carbonyl pyrrolidine-1-carboxylate (8), LCMS, (m/z) 457/459,($M^+$—$CO_2$($CH_3$)$_3$): tert-butyl 2-(4-bromobenzyl)-2-{[methoxy(methyl)amino]carbonyl}pyrrolidine-1-carboxylate (9), LCMS, (m/z) 449/451 ($M^+$+Na).

Preparations of (10)-(12) (infra)

The appropriate amide tert-butyl (4R)-2-(4-bromobenzyl)-4-{[tert-butyl(dimethyl)silyl]oxy}-2-{[methoxy(methyl)amino]carbonyl}pyrrolidine-1-carboxylate (8) or tert-butyl 2-(4-bromobenzyl)-2-{[methoxy(methyl)amino]carbonyl}pyrrolidine-1-carboxylate (9) (2 mmol) was suspended in anhydrous THF (5 mL) and treated with appropriate alkyl Grignard (5 mmol) ethylmagnesium bromide (5 mL, 1.0 M in THF) and cyclopropylmagnesium bromide (10 mL, 0.5 M in THF). The reactions were heated at reflux for 5 h (monitored by LCMS), cooled to rt., poured into water (25 mL), acidified to pH-2 using 1 N aq. HCl and extracted with $Et_2O$ (4×25 mL). The extracts are combined and washed with water (1×25 mL), sat. aqueous $NaHCO_3$ solution (25 mL), sat. aqueous NaCl solution (25 mL) and dried ($MgSO_4$). The solvents were removed in vacuo give the following products. Tert-butyl (4R)-2-(4-bromobenzyl)-4-{[tert-butyl(dimethyl)silyl]oxy}-2-propionylpyrrolidine-1-carboxylate (10), (90%, crude), LCMS, (m/z) 525/527 (M$^+$+H); tert-butyl 2-(4-bromobenzyl)-2-propionylpyrrolidine-1-carboxylate (11), (95%, crude), LCMS, (m/z) 396/398 (M$^+$+H); tert-butyl 2-(4-bromobenzyl)-2-(cyclopropylcarbonyl)pyrrolidine-1-carboxylate (12), (95%, crude), LCMS, (m/z) 408/410 (M$^+$+H).

Preparations of (13)-(15) (infra)

The respective ketone products tert-butyl (4R)-2-(4-bromobenzyl)-4-{[tert-butyl(dimethyl)silyl]oxy}-2-propionylpyrrolidine-1-carboxylate (10), tert-butyl 2-(4-bromobenzyl)-2-propionylpyrrolidine-1-carboxylate (11) or (tert-butyl 2-(4-bromobenzyl)-2-(cyclopropylcarbonyl)pyrrolidine-1-carboxylate (12) (1 mmol) were treated with 4 M solution of HCl in dioxane (10 mL). The reaction was stirred for 5 h and the solvent removed in vacuo. The resulting material was re-suspended in water (15 mL) and 1 N aqueous HCl (2 mL) and extracted with diethyl ether (2×10 mL). The aqueous layer was basified with solid NaHCO$_3$ to pH-8 and extracted with DCM (4×15 mL). The DCM extracts were combined, washed with sat. aqueous NaCl solution (10 mL) and dried (MgSO$_4$). Solvent was removed in vacuo to give which were used as such for the subsequent step without further purification. 1-[(4R)-2-(4-bromobenzyl)-4-hydroxypyrrolidin-2-yl]propan-1-one (13), LCMS, (m/z) 311/313 (M$^+$+H); 1-[2-(4-bromobenzyl)pyrrolidin-2-yl]propan-1-one (14), LCMS, (m/z) 296/298 (M$^+$+H); ([2-(4-bromobenzyl)pyrrolidin-2-yl](cyclopropyl)methanone (15), LCMS, (m/z) 308/310 (M$^+$+H).

Preparations of (16)-(18)(infra)

The appropriate proline derivative 1-[(4R)-2-(4-bromobenzyl)-4-hydroxypyrrolidin-2-yl]propan-1-one (13), 1-[2-(4-bromobenzyl)pyrrolidin-2-yl]propan-1-one 14 or [2-(4-bromobenzyl)pyrrolidin-2-yl](cyclopropyl)methanone (15) (0.5 mmol) was suspended in DMF (3 mL) and treated sequentially with 3,5-dichlorophenyl acetic acid (115 mg, 0.55 mmol), EDCI (105 mg, 0.55 mmol) and DIPEA (265 ul, 1.5 mmol). The reaction was stirred for 20 h at rt. poured into water (50 mL) and extracted with Et$_2$O (4×25 mL). The extracts are combined and washed sequentially with aqueous 1N HCl (2×15 mL), aqueous sat. NaHCO$_3$ solution (1×25 mL), aqueous sat. NaCl solution (1×25 mL), and dried (MgSO$_4$). Solvent was removed in vacuo to give product that was used in the subsequent step without purification. 1-{(4R)-2-(4-bromobenzyl)-1-[(3,5-dichlorophenyl)acetyl]-4-hydroxypyrrolidin-2-yl}propan-1-one (16), LCMS, (m/z) 517.9/519.9 (M$^+$+Na$^+$); (1-{2-(4-bromobenzyl)-1-[(3,5-dichlorophenyl)acetyl]pyrrolidin-2-yl}propan-1-one (17), LCMS, (m/z) 482/484 (M$^+$+H); {2-(4-bromobenzyl)-1-[(3,5-dichlorophenyl)acetyl]pyrrolidin-2-yl}(cyclopropyl)methanone (18), LCMS, (m/z) 494/496 (M$^+$+H).

Preparations of (19) and (20) (infra)

The appropriate N-Boc Proline methyl ester 1-tert-butyl 2-methyl (4R)-4-{[tert-butyl(dimethyl)silyl]oxy}-2-(4-cyanobenzyl)pyrrolidine-1,2-dicarboxylate (5) or 1-tert-butyl 2-methyl 2-(4-cyanobenzyl)pyrrolidine-1,2-dicarboxylate (7), (5 mmol) was treated with 4 N HCl in dioxane (25 mL). The reaction was stirred for 5 h and the solvent removed in vacuo. The resulting material was re-suspended in water (20 mL) and 1 N aqueous HCl (5 mL) and extracted with diethyl ether (2×30 mL). The aqueous layer was basified with solid NaHCO$_3$ to pH-8 and extracted with DCM (4×30 mL). The DCM extracts were combined, washed with sat. aqueous NaCl solution (25 mL) and dried (MgSO$_4$). Solvent was removed in vacuo to give the desired products which was used as such for subsequent steps without purification. Methyl (4S)-2-(4-cyanobenzyl)-4-hydroxypyrrolidine-2-carboxylate (19) (1.1 g, 85%), LCMS, (m/z) 261 (M$^+$+H); methyl 2-(4-cyanobenzyl)pyrrolidine-2-carboxylate (20) (1 g, 85%), LCMS, (m/z) 245 (M$^+$+H).

Preparations of (21) and (22) (infra)

The appropriate proline derivative, methyl (4S)-2-(4-cyanobenzyl)-4-hydroxypyrrolidine-2-carboxylate (19) or methyl 2-(4-cyanobenzyl)pyrrolidine-2-carboxylate (20), (1 mmol) was suspended in DMF (5 mL) and treated sequentially with 3,5-dichlorophenyl acetic acid (215 mg, 1.05 mmol), EDCI (307 mg, 1.05 mmol) and DIPEA (440 uL, 2.5 mmol). The reaction mixture was stirred for 20 h at rt., poured into water (50 mL) and extracted with Et$_2$O (4×25 mL). The extracts are combined and washed sequentially with aqueous 1N HCl (2×25 mL), aqueous sat. NaHCO$_3$ solution (1×25 mL), aqueous sat. NaCl solution (1×25 mL), and dried (MgSO$_4$). Solvent was removed in vacuo to products that were used in the subsequent step without purification. Methyl (4R)-2-(4-cyanobenzyl)-1-[(3,5-dichlorophenyl)acetyl]-4-hydroxypyrrolidine-2-carboxylate 21 (290 mg, 65%), LCMS, (m/z) 446 (M$^+$+H); methyl 2-(4-cyanobenzyl)-1-[(3,5-dichlorophenyl)acetyl]pyrrolidine-2-carboxylate (22) (430 mg, crude 100%) MS, (m/z) 431 (M$^+$+H).

Preparation of (23) (infra)

A 4-Hydroxy-L-proline derivative, methyl (4R)-2-(4-cyanobenzyl)-1-[(3,5-dichlorophenyl)acetyl]-4-hydroxypyrrolidine-2-carboxylate 21 (10 mmol) and imidazole (1.5 g, 22.5 mmol) were suspended in DMF (25 mL) and treated with tert-butyl(dimethyl)silyl chloride (1.6 g, 10.5 mmol). The reaction was stirred for 20 h, poured into water (100 mL) and extracted with diethyl ether (Et$_2$O) (4×30 mL). The organic extracts were combined and washed with 1N HCl aq. (2×30 mL), water (1×50 mL), sat. aqueous NaHCO$_3$ solution (1×30 mL) and sat. aq. NaCl solution (1×30 mL). The organic layer was dried (MgSO$_4$) and solvent removed in vacuo to give methyl (4R)-4-{[tert-butyl(dimethyl)silyl]oxy}-2-(4-cyanobenzyl)-1-[(3,5-dichlorophenyl)acetyl]pyrrolidine-2-carboxylate (23) (~5 g, 90%), which was used as such in subsequent reaction without further purification, LCMS, (m/z) 561 (M$^+$+H).

Preparations of (24) and (25) (infra)

Methyl 2-(4-cyanobenzyl)-1-[(3,5-dichlorophenyl)acetyl]pyrrolidine-2-carboxylate (22) or methyl (4R)-4-{[tert-butyl(dimethyl)silyl]oxy}-2-(4-cyanobenzyl)-1-[(3,5-dichlorophenyl)acetyl]pyrrolidine-2-carboxylate 23 (0.5 mmol) was suspended in dry THF (5 mL), cooled to -78° C. and treated with LHMDS, 1 M in THF, (1 mL, 1 mmol). The dry ice bath was removed and the reaction stirred for 30 min at rt. The contents were poured into water (20 mL), acidified to pH 2 with aqueous 1N HCl and extracted with Et$_2$O (4×20 mL). The extracts were combined, washed with sat. aqueous NaCl solution (10 mL), and dried (MgSO$_4$). The solvent was removed in vacuo and the cyclized products were used in the subsequent reaction without further purification. 4-{[6-(3,5-Dichlorophenyl)-7-hydroxy-5-oxo-2,3-dihydro-1 H-pyrrolizin-7a(5H)-yl]methyl}benzonitrile (24) (185mg), LCMS (m/z) 399 (M$^+$+H); 4-{[(2R)-2-{[tert-butyl(dimethyl)silyl]oxy} -6-(3,5-dichlorophenyl)-7-hydroxy-5-oxo-2,3-dihydro-1H-pyrrolizin-7a(5H)-yl]methyl}benzonitrile (25) (-294 mg, diasteromeric mixture) LCMS, (m/z) 529/530 ($M^++H$).

Preparations of (26)-(28) (infra)

The appropriate enol-lactam 4-{[6-(3,5-dichlorophenyl)-7-hydroxy-5-oxo-2,3-dihydro-1H-pyrrolizin-7a(5H)-yl]methyl}benzonitrile (24) or 4-{[(2R)-2-{[tert-butyl(dimethyl)silyl]oxy}-6-(3,5-dichlorophenyl)-7-hydroxy-5-oxo-2,3-dihydro-1H-pyrrolizin-7a(5H)-yl]methyl}benzonitrile (25) (0.15 mmol) was suspended in DCE (10 mL) and cooled to −10° C. DIPEA (55 µL, 0.3 mmol) was added followed by the drop wise addition of trifluoromethylsulfonic acid anhydride ($Tf_2O$) (40 µl, 0.23 mmol). The ice bath was removed and the reaction was stirred for 2 h at room temperature. Water (10 ml) and $Et_2O$ (20 mL) were added and the organic layer isolated. The aqueous layer was further extracted with $Et_2O$ (3×20 mL). The extracts were combined and washed with 0.25 N aqueous HCl (2×10 mL), water (1×10 mL), sat. aqueous $NaHCO_3$ solution (1×10 mL), sat. aqueous NaCl solution (1×10 mL) and dried ($MgSO_4$). Solvent was removed in vacuo and the residue purified using silica gel chromatography. 7a-(4-Cyanobenzyl)-6-(3,5-dichlorophenyl)-5-oxo-2,3,5,7a-tetrahydro-1H-pyrrolizin-7-yl trifluoromethanesulfonate (26) (50 mg, 60%, from (24)), LCMS (m/z) 531/533 ($M^++H$); (2R)-2-{[tert-butyl(dimethyl)silyl]oxy}-7a-(4-cyanobenzyl)-6-(3,5-dichlorophenyl)-5-oxo-2,3,5,7a-tetrahydro-1H-pyrrolizin-7-yl trifluoromethanesulfonate (diastereomer #5) (27) (-30%, first eluted isomer on silica, from (25)), LCMS (m/z) 661($M^++H$); (2R)-2-{[tert-butyl(dimethyl)silyl]oxy}-7a-(4-cyanobenzyl)-6-(3,5-dichlorophenyl)-5-oxo-2,3,5,7a-tetrahydro-1H-pyrrolizin-7-yl trifluoromethanesulfonate (diastereomer #6) (28) (-50%, second eluted isomer on silica from (25)), LCMS (m/z) 661 ($M^++H$); .

Preparation of (29) (infra)

(2R)-2-{[tert-butyl(dimethyl)silyl]oxy}-7a-(4-cyanobenzyl)-6-(3,5-dichlorophenyl)-5-oxo-2,3,5,7a-tetrahydro-1H-pyrrolizin-7-yl trifluoromethanesulfonate (diastereomer #6) (28) (50 mg, 0.075 mmol), $Zn(CN)_2$ (18 mg, 0.152 mmol) and $Pd(PPh_3)_4$ (9 mg, 0.008 mmol, 10 mol%) were suspended in DMF (2.5 mL) and the microwave vessel sealed with a septum. DIPEA (25 µl, 0.15 mmol) was added and the vessel purged with nitrogen gas. The vessel was placed in a Personal Chemistry microwave™ and heated at 195° C. for 10 min. The reaction mixture was diluted with MeOH (1.5 mL) and purified using preparative HPLC. (2R)-2-{[tert-Butyl(dimethyl)silyl]oxy}-7a-(4-cyanobenzyl)-6-(3,5-dichlorophenyl)-5-oxo-2,3,5,7a-tetrahydro-1H-pyrrolizine-7-carbonitrile (29) (30mg, 74%), LCMS, (m/z) 538 ($M^++H$).

EXAMPLES I-IV 7a-(4-Bromobenzyl)-2-(3,5-dichlorophenyl)-1-ethyl-5,6,7,7a-tetrahydro-3H-pyrrolizin-3-one 1,7a-(4-Bromobenzyl)-1-cyclopropyl-2-(3,5-dichlorophenyl)-5,6,7,7a-tetrahydro-3H-pyrrolizin-3-one.II, (6R)-7a-(4-Bromobenzyl)-2-(3,5-dichlorophenyl)-1-ethyl-6-hydroxy-5,6,7,7a-tetrahydro-3H-pyrrolizin-3-one.III, (6R)-7a-(4-Bromobenzyl)-2-(3,5-dichlorophenyl)-1-ethyl-6-hydroxy-5,6,7,7a-tetrahydro-3H-pyrrolizin-3-one IV Respective proline ketones 1-{(4R)-2-(4-bromobenzyl)-1-[(3,5-dichlorophenyl)acetyl]-4-hydroxypyrrolidin-2-yl}propan-1-one (16), (1-{2-(4-bromobenzyl)-1-[(3,5-dichlorophenyl)acetyl]pyrrolidin-2-yl}propan-1-one (17), or 2-(4-bromobenzyl)-1-[(3,5-dichlorophenyl)acetyl]pyrrolidin-2-yl}(cyclopropyl)methanone (18), (0.25 mmol) was suspended in 5% KOH in EtOH (2 mL). The reaction was heated at 85° C. for 1 h, cooled to rt., poured into water (10 mL) and extracted with $Et_2O$ (4×10 mL). The extracts were combined, washed with aqueous 1N HCl (10 mL), sat. aqueous $NaHCO_3$ solution (10 mL), sat. aqueous NaCl solution (10 mL), and dried ($MgSO_4$). The solvent was removed in vacuo and the product purified using Prep HPLC or silica gel chromatography. 7a-(4-Bromobenzyl)-2-(3,5-dichlorophenyl)-1-ethyl-5,6,7,7a-tetrahydro-3H-pyrrolizin-3-one I, (80%, from crude (17)), LCMS, (m/z) 464/465 ($M^++H$); HPLC Retention Time/Condition 1: 2.15 min. 7a-(4-Bromobenzyl)-1-cyclopropyl-2-(3,5-dichlorophenyl)-5,6,7,7a-tetrahydro-3H-pyrrolizin-3-one II, (80% from crude (18)), LCMS, (m/z) 476/478 ($M^++H$). HPLC Retention Time/Condition 1: 2.12 min. III/IV (60% from crude (16), 60/40 diastereomeric mixture), individual diastereomer separated by reverse phase preparative HPLC. (6R)-7a-(4-Bromobenzyl)-2-(3,5-dichlorophenyl)-1-ethyl-6-hydroxy-5,6,7,7a-tetrahydro-3H-pyrrolizin-3-one III, LCMS, (m/z) 479/482 ($M^++H$); HPLC Retention Time/Condition 3:3.57 min. (6R)-7a-(4-Bromobenzyl)-2-(3,5-dichlorophenyl)-1-ethyl-6-hydroxy-5,6,7,7a-tetrahydro-3H-pyrrolizin-3-one IV, LCMS, (m/z) 479/482 ($M^++H$); HPLC Retention Time/Condition 3:3.64 min.

EXAMPLES V AND VI

4-{[6-(3 5-Dichlorophenyl)-7-ethyl-5-oxo-2,3-dihydro-1H-pyrrolizin-7a(5H)-yl]methyl}benzonitrile V, 4-{[(2R)-6-(3,5-Dichlorophenyl)-7-ethyl-2-hydroxy-5-oxo-2,3-dihydro-1H-pyrrolizin-7a(5H)-yl] methyl}benzonitrile VI Aryl bromide, 7a-(4-Bromobenzyl)-2-(3,5-dichlorophenyl)-1-ethyl-5,6,7,7a-tetrahydro-3H-pyrrolizin-3-one I. Or (6R)-7a-(4-Bromobenzyl)-2-(3,5-dichlorophenyl)-1-ethyl-6-hydroxy-5,6,7,7a-tetrahydro-3H-pyrrolizin-3-one III (0.1 mmol), $Zn(CN)_2$ (23 mg, 0.2 mmol) and $Pd(PPh_3)_4$ (6 mg, 0.05eq) were transferred to a microwave tube and suspended in DMF (1 mL). The vessel was sealed and degassed, purged with nitrogen and heated using the Personal Chemistry® microwave at 200° C. for 15 min. The reaction mixture was diluted with MeOH (2 mL), filtered through a plug of Celite, and purified using preparative reverse phase HPLC using a $MeOH/H_2O/TFA(0.1\%)$ solvent system. 4-{[6-(3,5-Dichlorophenyl)-7-ethyl-5-oxo-2,3-dihydro-1H-pyrrolizin-7a (5H)-yl]methyl benzonitrile V, (70%), LCMS, (m/z) 411/413 ($M^++H$) HPLC Retention Time/Condition 1:2.03 min.; 4-{[(2R)-6-(3,5-Dichlorophenyl)-7-ethyl-2-hydroxy-5-oxo-2,3-dihydro-1H-pyrrolizin-7a(5H)-yl]methyl}benzonitrile VI, (60%), LCMS, (m/z) 427/429 ($M^++H$) HPLC Retention Time/Condition 1: 1.79 min.

EXAMPLES VIIa AND VIIb (2S,7aR)-7a-(4-bromobenzyl)-6-(3,5-dichlorophenyl)-7-ethyl-5-oxo-2,3,5,7a-tetrahydro-1H-pyrrolizin-2-yl benzoate VIIa, (2S,7aS)-7a-(4-Bromobenzyl)-6-(3,5-dichlorophenyl)-7-ethyl-5-oxo-2,3,5,7a-tetrahydro-1H-pyrrolizin-2-yl benzoate VIIb Diastereomeric mixture of III and IV, (6R)-7a-(4-Bromobenzyl)-2-(3,5-dichlorophenyl)-1-ethyl-6-hydroxy-5,6,7,7a-tetrahydro-3H-pyrrolizin-3-one, (200 mg, 0.415 mmol), benzoic acid (61 mg, 0.5 mmol) and $PPh_3$ (130 mg, 0.5 mmol) were suspended in dry THF (3 mL) and treated with DIAD (diisopropylazodicarboxylate). The reaction was stirred overnight (18 h). TLC show the complete separation of the two diastereomers (2S,7aR)-7a-(4-bromobenzyl)-6-(3,5-dichlorophenyl)-7-ethyl-5-oxo-2,3,5,7a-tetrahydro-1H-pyrrolizin-2-yl benzoate VIIa and (2S,7aS)-7a-(4-bromobenzyl)-6-(3,5-dichlorophenyl)-7-ethyl-5-oxo-2,3,5,7a-tetrahydro-1H-pyrrolizin-2-yl benzoate VIb. Solvent was removed in vacuo and the material chromatographed on Silica gel with 20% EtOAc/heptane to give individual enatiomers. VIIa (130 mg, 54%, first eluted isomer) LCMS, (m/z) 584/586 (M$^+$+H), HPLC Retention Time/Condition 2: 4.14 min and VIIb (80 mg, 32%, second eluted isomer) LCMS, (m/z) 584/586 (M$^+$+H), HPLC Retention Time/Condition 2: 4.05 min Absolute structural stereochemistry was assigned using 2D NOESY experiments.

EXAMPLE VIII (6S, 7aS)-7a-(4-Bromobenzyl)-2-(3.5-dichlorophenyl)-1-ethyl-6-hydroxy-5,6,7,7a-tetrahydro-3H-pyrrolizin-3-one VIII (2S,7aS)-7a-(4-Bromobenzyl)-6-(3,5-dichlorophenyl)-7-ethyl-5-oxo-2,3,5,7a-tetrahydro-1H-pyrrolizin-2-yl benzoate VIIb (5 mg, 0.01 mmol) was suspended in THF (1 mL) and treated with 1N aqueous NaOH (50 uL). The reaction was stirred for 5 h, diluted with MeOH (1 mL) and purified on preparative HPLC using MeOH, H$_2$O, TFA(0.1%) as the eluant to give (6S, 7aS)-7a-(4-Bromobenzyl)-2-(3,5-dichlorophenyl)-1-ethyl-6-hydroxy-5,6,7,7a-tetrahydro-3H-pyrrolizin-3-one VIII, (2 mg, 42%) LCMS, (m/z) 480/482 (M$^+$+H), HPLC Retention Time/Condition 1: 2.03 min.

EXAMPLE IX

4-{[6-(3,5-Dichlorophenyl)-7-methyl-5-oxo-2,3-dihydro-1H-pyrrolizin-7a(5H)-yl]methyl}benzonitrile IX To a suspension of CuCN (22.5 mg, 0.25 mmol) in dry THF (2 ML) at −78° C., under nitrogen atmosphere, was added a solution of MeLi in Et$_2$O (1.4 M, 0.37 mL, 0.5 mmol). The mixture was stirred for 30 min and treated drop wise with a solution of 7a-(4-cyanobenzyl)-6-(3,5-dichlorophenyl)-5-oxo-2,3,5,7a-tetrahydro-1H-pyrrolizin-7-yl trifluoromethanesulfonate 26 (50 mg, 0.09 mmol) in THF (1 mL). The reaction was stirred for 2 h at −78° C. and 20 min. at −20° C. The reaction was treated with 10% aqueous NH$_4$OH (10 ml), stirred at rt. for 10 min. and extracted with Et$_2$O (4×10 mL). The extracts were combined sat. NaCl solution (10 ml), dried (MgSO$_4$) and solvent removed. The resulting oil was purified using preparative HPLC to give 4-{[6-(3,5-Dichlorophenyl)-7-methyl-5-oxo-2,3-dihydro-1H-pyrrolizin-7a(5H)-yl]methyl}benzonitrile IX (5 mg, 14%), LCMS (m/z) 397/399 (M$^+$+H), HPLC Retention Time/Condition 1: 1.86 min.

EXAMPLES Xa AND Xb 7a-(4-Cyanobenzyl)-6-(3,5-dichlorophenyl)-5-oxo-2,3,5,7a-tetrahydro-1H-pyrrolizine-7-carbonitrile.Xa, 7a-(4-Cyanobenzyl)-6-(3,5-dichlorophenyl)-5-oxo-2,3,5,7a-tetrahydro-1H-pyrrolizine-7-carbonitrile Xb 7a-(4-Cyanobenzyl)-6-(3,5-dichlorophenyl)-5-oxo-2,3,5,7a-tetrahydro-1H-pyrrolizin-7-yl trifluoromethanesulfonate (26) (120 mg, 0.226 mmol), Zn(CN)$_2$ (50 mg, 0.427 mmol) and Pd(PPh$_3$)$_4$ (15 mg, 0.013 mmol, 5.7 mol %) were suspended in DMF (3 mL) and the microwave vessel sealed with a septum. DIPEA (105 μl, 0.6 mmol) was added and the vessel purged with nitrogen gas. The vessel was placed in a Personal Chemistry microwave™ and heated at 195° C. for 10 min. The reaction mixture was diluted with MeOH (3 mL) and purified using preparative HPLC. Racemic mixture of 7a-(4-cyanobenzyl)-6-(3,5-dichlorophenyl)-5-oxo-2,3,5,7a-tetrahydro-1H-pyrrolizine-7-carbonitrile Xa/Xb was recovered in combined yield of 44% (40 mg) with LCMS (m/z) 408/410 (M$^+$+H). Individual enatiomers were resolved using chiral preparative HPLC Chiralpak AD 2×50 cm column using a isocratic 15% [EtOH/MeOH(1/1)]/heptane solvent system; flow rate 15 ml/min. Xa (enantiomer #1) eluted with a retention time 28.3 min. while entiomer Xb (entiomer #2) eluted with a retension time 34 min. Furthermore, enatiomer Xa exhibited a retension time of 11.57 min using conditions 4, while Xb exhibited a retension time of 14.00 min using conditions 4.

EXAMPLE XI (2R)-7a-(4-cyanobenzyl)-6-(3,5-dichlorophenyl)-2-hydroxy-5-oxo-2,3,5,7a-tetrahydro-1H-pyrrolizine-7-carbonitrile XII The O-silyl ether (2R)-2-{[tert-butyl(dimethyl)silyl]oxy}-7a-(4-cyanobenzyl)-6-(3,5-dichlorophenyl)-5-oxo-2,3,5,7a-tetrahydro-1H-pyrrolizine-7-carbonitrile (29) (15 mg, 0.023 mmol) was suspended in 1/1 DCE/TFA (2 mL) and stirred at room temperature for 20 h. Solvent was removed in vacuo and the oil purified using preparative HPLC to give (2R)-7a-(4-cyanobenzyl)-6-(3,5-dichlorophenyl)-2-hydroxy-5-oxo-2,3,5,7a-tetrahydro-1H-pyrrolizine-7-carbonitrile XI (7 mg, 72%), ), LCMS, (m/z) 424 (M$^+$+H), HPLC Retention Time/Condition 1: 1.79 min

EXAMPLE XII

4-[6-(3,5-Dichloro-phenyl)-7-methoxy-5-oxo-2,3-dihydro-1H,5H-pyrrolizin-7 a-ylmethyl]-benzonitrile XII 4-[6-(3,5-Dichloro-phenyl)-7-hydroxy-5-oxo-2,3-dihydro-1H,5H-pyrrolizin-7a-ylmethyl]-benzonitrile (24), (60 mg, 0.15 mmol) Trimethyl phosphate (4 ml) and K$_2$CO$_3$ were stirred under reflux for 10 hours then cooled to RT and diluted with water. The precipitate was filtered to afford after HPLC purification 4-[6-(3,5-Dichloro-phenyl)-7-methoxy-5-oxo-2,3-dihydro-1H,5H-pyrrolizin-7a-ylmethyl]-benzonitrile XII (18mg) as a white solid.

$^1$H-NMR (CDCl$_3$, 200 MHz): 1.85-2.05 (2H, m), 2.1-2.3 (2H, m), 3.1 (2H, s), 3.15-3.3 (1H, m), 3.7 (3H, s), 3.7-3.9 (1H, m), 6.9 (2H, m), 7.2-7.4 (3H, m), 7.6 (2H, d).

What is claimed is:

1. A compound having the structure of formula (Ic):

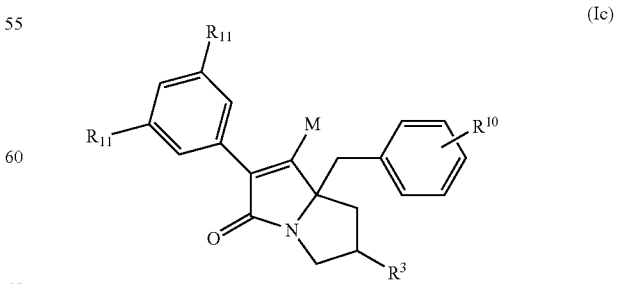

or a pharmaceutically-acceptable salt, enantiomer, or diastereomer, thereof wherein:

M is methyl, ethyl, propyl, cyclopropyl, or $CF_3$;
$R^3$ is hydroxy or —OC(=O)phenyl;
$R^{10}$ is chloro, fluoro, bromo, or cyano; and
$R^{11}$ independently at each occurrence is chloro, fluoro, or bromo.

2. The compound of claim 1, or a pharmaceutically-acceptable salt, enantiomer, or diastereomer thereof, in which each $R^{11}$ is chloro.

3. A compound selected from
(i)
7a-(4-Bromobenzyl)-2-(3,5-dichlorophenyl)-1-ethyl-5,6,7,7a-tetrahydro-3H-pyrrolizin-3-one;

7a-(4-Bromobenzyl)-1-cyclopropyl-2-(3,5-dichlorophenyl)-5,6,7,7a-tetrahydro-3H-pyrrolizin-3-one;

(6R)-7a-(4-Bromobenzyl)-2-(3,5-dichlorophenyl)-1-ethyl-6-hydroxy-5,6,7,7a-tetrahydro-3H-pyrrolizin-3-one;

(6R)-7a-(4-Bromobenzyl)-2-(3,5-dichlorophenyl)-1-ethyl-6-hydroxy-5,6,7,7a-tetrahydro-3H-pyrrolizin-3-one;

4-{[6-(3,5-Dichlorophenyl)-7-ethyl-5-oxo-2,3-dihydro-1H-pyrrolizin-7a(5H)-yl]methyl}benzonitrile;

4-{[(2R)-6-(3,5-Dichlorophenyl)-7-ethyl-2-hydroxy-5-oxo-2,3-dihydro-1H-pyrrolizin-7a(5H)-yl]methyl}benzonitrile;

(2S,7aR)-7a-(4-bromobenzyl)-6-(3,5-dichlorophenyl)-7-ethyl-5-oxo-2,3,5,7a-tetrahydro-1H-pyrrolizin-2-yl benzoate;

(2S,7aS)-7a-(4-Bromobenzyl)-6-(3,5-dichlorophenyl)-7-ethyl-5-oxo-2,3,5,7a-tetrahydro-1H-pyrrolizin-2-yl benzoate;

(6S, 7aS)-7a-(4-Bromobenzyl)-2-(3,5-dichlorophenyl)-1-ethyl-6-hydroxy-5,6,7,7a-tetrahydro-3H-pyrrolizin-3-one;

4-{[6-(3,5-Dichlorophenyl)-7-methyl-5-oxo-2,3-dihydro-1H-pyrrolizin-7a(5H)-yl]methyl}benzonitrile;

4-{[6-(3,5-Dichlorophenyl)-7-methyl-5-oxo-2,3-dihydro-1H-pyrrolizin-7a(5H)-yl]methyl}benzonitrile;

7a-(4-Cyanobenzyl)-6-(3,5-dichlorophenyl)-5-oxo-2,3,5,7a-tetrahydro-1H-pyrrolizine-7-carbonitrile;

7a-(4-Cyanobenzyl)-6-(3,5-dichlorophenyl)-5-oxo-2,3,5,7a-tetrahydro-1H-pyrrolizine-7-carbonitrile;

(2R)-7a-(4-cyanobenzyl)-6-(3,5-dichlorophenyl)-2-hydroxy-5-oxo-2,3,5,7a-tetrahydro-1H-pyrrolizine-7-carbonitrile; and 4-[6-(3,5-Dichloro-phenyl)-7-methoxy-5-oxo-2,3-dihydro-1H,5H-pyrrolizin-7a-ylmethyl]-benzonitrile; or (ii) a pharmaceutically-acceptable salt, enantiomer, or diastereomer of (i), thereof.

4. A pharmaceutical composition comprising (a) at least one compound according to claim 1, or a pharmaceutically acceptable salt thereof, and (b) a pharmaceutically acceptable carrier or diluent.

5. A method of treating comprising: administering to the mammal in need of such treatment a therapeutically-effective amount of a compound according to claim 1.

* * * * *